(12) United States Patent
Hourtash et al.

(10) Patent No.: US 9,517,106 B2
(45) Date of Patent: Dec. 13, 2016

(54) SYSTEMS AND METHODS FOR COMMANDED RECONFIGURATION OF A SURGICAL MANIPULATOR USING THE NULL-SPACE

(71) Applicant: Intuitive Surgical Operations, Inc., Sunnyvale, CA (US)

(72) Inventors: Arjang M. Hourtash, Santa Clara, CA (US); Paul W. Mohr, Mountain View, CA (US); Pushkar Hingwe, Fremont, CA (US); Paul Millman, San Jose, CA (US); Bruce Michael Schena, Menlo Park, CA (US); Roman L. Devengenzo, San Jose, CA (US); Scott Luke, Ben Lomond, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 76 days.

(21) Appl. No.: 13/906,767

(22) Filed: May 31, 2013

(65) Prior Publication Data

US 2014/0358161 A1    Dec. 4, 2014

Related U.S. Application Data

(60) Provisional application No. 61/654,764, filed on Jun. 1, 2012.

(51) Int. Cl.
*G06F 19/00* (2011.01)
*A61B 19/00* (2006.01)

(52) U.S. Cl.
CPC .......... *A61B 19/2203* (2013.01); *A61B 34/30* (2016.02); *A61B 34/37* (2016.02); *Y10S 901/15* (2013.01)

(58) Field of Classification Search
CPC combination set(s) only.
See application file for complete search history.

(56) References Cited

U.S. PATENT DOCUMENTS 3,920,972 A   11/1975  Corwin, Jr. et al.
4,028,533 A    6/1977  Matsubara
              (Continued)

FOREIGN PATENT DOCUMENTS

CN     1155833 A     7/1997
EP     1234641 A1    8/2002
              (Continued)

OTHER PUBLICATIONS

"European Application Serial No. 10196664.6, Extended European Search Report mailed Jul. 25, 2012", 7 pgs.
(Continued)

*Primary Examiner* — Bhavesh V Amin

(57) ABSTRACT

Devices, systems, and methods for reconfiguring a surgical manipulator by moving the manipulator within a null-space of a kinematic Jacobian of the manipulator arm. In one aspect, in response to receiving a reconfiguration command, the system drives a first set of joints and calculates velocities of the plurality of joints to be within a null-space. The joints are driven according to the reconfiguration command and the calculated movement so as to maintain a desired state of the end effector or a remote center about which an instrument shaft pivots. In another aspect, the joints are also driven according to a calculated end effector or remote center displacing velocities within a null-perpendicular-space of the Jacobian so as to effect the desired reconfiguration concurrently with a desired movement of the end effector or remote center.

43 Claims, 23 Drawing Sheets

(56) References Cited

U.S. PATENT DOCUMENTS

| | | | |
|---|---|---|---|
| 4,063,073 A | 12/1977 | Strayer | |
| 4,578,757 A | 3/1986 | Stark | |
| 4,999,553 A | 3/1991 | Seraji | |
| 5,086,401 A | 2/1992 | Glassman et al. | |
| 5,130,632 A | 7/1992 | Ezawa et al. | |
| 5,159,249 A | 10/1992 | Megherbi | |
| 5,333,242 A * | 7/1994 | Watanabe et al. | 700/254 |
| 5,430,543 A | 7/1995 | Howard | |
| 5,513,100 A | 4/1996 | Parker et al. | |
| 5,550,953 A | 8/1996 | Seraji | |
| 5,587,937 A | 12/1996 | Massie et al. | |
| 5,632,758 A | 5/1997 | Sklar | |
| 5,710,870 A | 1/1998 | Ohm et al. | |
| 5,737,500 A | 4/1998 | Seraji et al. | |
| 5,823,980 A | 10/1998 | Kopfer | |
| 5,855,583 A | 1/1999 | Wang et al. | |
| 5,908,458 A | 6/1999 | Rowe et al. | |
| 6,037,927 A | 3/2000 | Rosenberg | |
| 6,098,260 A | 8/2000 | Sarh | |
| 6,246,200 B1 | 6/2001 | Blumenkranz et al. | |
| 6,312,435 B1 | 11/2001 | Wallace et al. | |
| 6,317,651 B1 | 11/2001 | Gerstenberger et al. | |
| 6,331,181 B1 | 12/2001 | Tierney et al. | |
| 6,377,011 B1 | 4/2002 | Ben-Ur | |
| 6,379,073 B1 | 4/2002 | Yoo et al. | |
| 6,400,115 B1 | 6/2002 | Yamazoe | |
| 6,424,885 B1 | 7/2002 | Niemeyer et al. | |
| 6,459,926 B1 | 10/2002 | Nowlin et al. | |
| 6,468,265 B1 | 10/2002 | Evans et al. | |
| 6,493,608 B1 | 12/2002 | Niemeyer | |
| 6,645,196 B1 | 11/2003 | Nixon et al. | |
| 6,678,582 B2 | 1/2004 | Waled | |
| 6,699,177 B1 | 3/2004 | Wang et al. | |
| 6,763,286 B2 | 7/2004 | Metelski | |
| 6,786,896 B1 | 9/2004 | Madhani et al. | |
| 7,083,571 B2 | 8/2006 | Wang et al. | |
| 7,280,633 B2 | 10/2007 | Cheng et al. | |
| 7,379,533 B2 | 5/2008 | Koertge | |
| 7,428,296 B2 | 9/2008 | Bernhardt et al. | |
| 7,564,949 B2 | 7/2009 | Sattler et al. | |
| 7,763,015 B2 | 7/2010 | Cooper et al. | |
| 8,004,229 B2 | 8/2011 | Nowlin et al. | |
| 8,041,459 B2 | 10/2011 | Sutherland et al. | |
| 8,123,740 B2 | 2/2012 | Madhani et al. | |
| 8,162,926 B2 | 4/2012 | Schena | |
| 2001/0013764 A1 | 8/2001 | Blumenkranz et al. | |
| 2001/0018591 A1 | 8/2001 | Brock et al. | |
| 2002/0082612 A1 | 6/2002 | Moll et al. | |
| 2002/0111713 A1 | 8/2002 | Wang et al. | |
| 2002/0120363 A1 | 8/2002 | Salisbury et al. | |
| 2002/0128552 A1 * | 9/2002 | Nowlin | A61B 19/22 600/427 |
| 2003/0018412 A1 | 1/2003 | Kimura et al. | |
| 2003/0060927 A1 | 3/2003 | Gerbi et al. | |
| 2003/0065311 A1 | 4/2003 | Wang et al. | |
| 2003/0109780 A1 | 6/2003 | Coste-Maniere et al. | |
| 2003/0139753 A1 | 7/2003 | Wang et al. | |
| 2003/0216715 A1 | 11/2003 | Moll et al. | |
| 2004/0034283 A1 | 2/2004 | Quaid, III | |
| 2004/0039485 A1 | 2/2004 | Niemeyer et al. | |
| 2004/0042583 A1 | 3/2004 | Wackerle et al. | |
| 2004/0111183 A1 | 6/2004 | Sutherland et al. | |
| 2004/0186484 A1 | 9/2004 | Ryan | |
| 2005/0104549 A1 | 5/2005 | Nishimura et al. | |
| 2006/0178559 A1 * | 8/2006 | Kumar et al. | 600/109 |
| 2007/0013336 A1 * | 1/2007 | Nowlin et al. | 318/568.21 |
| 2007/0029117 A1 * | 2/2007 | Goldenberg et al. | 180/9.32 |
| 2007/0073442 A1 * | 3/2007 | Aghili | 700/245 |
| 2007/0142825 A1 * | 6/2007 | Prisco et al. | 606/1 |
| 2008/0033240 A1 * | 2/2008 | Hoffman et al. | 600/109 |
| 2008/0037712 A1 | 2/2008 | Klingenbeck-Regn | |
| 2008/0234864 A1 * | 9/2008 | Sugiura et al. | 700/255 |
| 2008/0312771 A1 * | 12/2008 | Sugiura | 700/259 |
| 2009/0234444 A1 | 9/2009 | Maschke | |
| 2009/0297011 A1 | 12/2009 | Brunner et al. | |
| 2010/0152899 A1 * | 6/2010 | Chang et al. | 700/262 |
| 2010/0191371 A1 | 7/2010 | Hornung et al. | |
| 2010/0280663 A1 * | 11/2010 | Abdallah et al. | 700/264 |
| 2011/0040306 A1 | 2/2011 | Prisco et al. | |
| 2011/0218679 A1 | 9/2011 | Cheng et al. | |
| 2011/0264108 A1 | 10/2011 | Nowlin et al. | |
| 2011/0264109 A1 | 10/2011 | Nowlin et al. | |
| 2011/0264110 A1 | 10/2011 | Nowlin et al. | |
| 2011/0264111 A1 | 10/2011 | Nowlin et al. | |
| 2011/0264112 A1 | 10/2011 | Nowlin et al. | |
| 2011/0270271 A1 | 11/2011 | Nowlin et al. | |
| 2011/0276059 A1 | 11/2011 | Nowlin et al. | |
| 2012/0095598 A1 * | 4/2012 | Nagasaka | 700/260 |
| 2013/0090763 A1 * | 4/2013 | Simaan et al. | 700/258 |
| 2013/0325030 A1 * | 12/2013 | Hourtash et al. | 606/130 |

FOREIGN PATENT DOCUMENTS

| | | |
|---|---|---|
| EP | 1430494 B1 | 1/2005 |
| GB | 2311149 A | 9/1997 |
| JP | 2003159674 A | 6/2003 |
| WO | 9729690 | 8/1997 |
| WO | 9950721 A1 | 10/1999 |
| WO | 02051329 A1 | 7/2002 |
| WO | 02060653 A9 | 12/2002 |
| WO | WO-2006124390 A2 | 11/2006 |
| WO | 2008015666 A2 | 2/2008 |
| WO | WO-2013078529 A1 | 6/2013 |

OTHER PUBLICATIONS

"European Application Serial No. 10196665.3, Extended European Search Report mailed Oct. 15, 2012", 8 pgs.

"European Application Serial No. 10196666.1, Extended European Search Report mailed Jul. 19, 2012", 7 pgs.

"European Application Serial No. 10196669.5, Extended European Search Report mailed Jul. 26, 2012", 7 pgs.

"European Application Serial No. 10196670.3, Extended European Search Report mailed Oct. 26, 2012", 9 pgs.

"European Application Serial No. 10196671.0, Extended European Search Report mailed Oct. 15, 2012", 7 pgs.

"International Application Serial No. PCT/US2006/017843, International Search Report mailed Jan. 4, 2007", 5 pgs.

"International Application Serial No. PCT/US2006/017843, Written Opinion mailed Jan. 4, 2007", 8 pgs.

"International Application Serial No. PCT/US2013/043557, International Search Report mailed Sep. 6, 2013", 6 pgs.

"International Application Serial No. PCT/US2013/043557, Written Opinion mailed Sep. 6, 2013", 7 pgs.

"International Application Serial No. PCT/US2013/043564, International Search Report mailed Sep. 6, 2013", 6 pgs.

"International Application Serial No. PCT/US2013/043564, Written Opinion mailed Sep. 6, 2013", 8 pgs.

"International Application Serial No. PCT/US2013/043578, International Search Report mailed Sep. 5, 2013", 7 pgs.

"International Application Serial No. PCT/US2013/043578, Written Opinion mailed Sep. 5, 2013", 5 pgs.

Albu-Schaffer A., et al., "Cartesian Impedance Control Techniques for Torque Controlled Light-Weight Robots," Proceedings of the 2002 IEEE, International Conference on Robotics and Automation, 2002, pp. 657-663.

Albu-Schaffer A., et al., "Parameter Identification and Passivity Based Joint Control for a 7DOF Torque Controlled Light Weight Robot," Proceedings of the 2001 IEEE, International Conference on Robotics and Automation, 2001, vol. 3, pp. 2852-2858.

Baerlocher, P. et al., "Task Priority Formulations for the Kinematic Control of Highly Redundant Articulated Structures," IEEE/RSJ International Conference on Intelligent Robots and Systems, 1998, pp. 323-329, vol. 1, IEEE.

Boyd, Stephen, "Convex Optimization," 2004, 8 pages, Cambridge University Press.

Da Vinci, Chirurgie-System Benutzerhandbuch, Intuitive Surgical Inc., 2004, 9 Chapters and 2 Appendixes, 260 pages.

(56) References Cited

OTHER PUBLICATIONS

English, James D. et al., "On the Implementation of Velocity Control for Kinematically Redundant Manipulators," IEEE transactions on systems, man, and cybernetics. Part A, Systems and humans, 2000, pp. 233-237, vol. 30—No. 3, IEEE.
Espiau, Bernard et al., "Collision Avoidance for Redundant Robots with Proximity Sensors," The Third International Symposium of Robotics Research, 1986, pp. 243-251, MIT Press.
European Search Report for Application No. EP10196665.3, mailed on Oct. 15, 2012, 8 pages.
European Search Report for Application No. EP10196666, mailed on Jul. 19, 2012, 7 pages.
European Search Report for Application No. EP10196670.3 , mailed Oct. 26, 2012, 9 pages.
European Search Report for Application No. EP10196671, mailed on Oct. 15, 2012, 7 pages.
Extended EP Search Report and Written Opinion for Application No. EP10196669.5, mailed Jul. 26, 2012, 7 pages.
Extended European Search Report and Written Opinion for Application No. EP10196664.6, mailed on Jul. 25, 2012, 7 pages.
Extended European Search Report for Application No. EP101996666.1, mailed on Jul. 19, 2012, 7 pages.
Grunwald G., et al., "Programming by Touch: The Different Way of Human-Robot Interaction," IEEE Transactions on Industrial Electronics, 2003, vol. 50 (4), pp. 659-666.
Hirzinger G., et al., "A Mechatronics Approach to the Design of Light-Weight Arms and Multifingered Hands," Proceedings of the 2000 IEEE, International Conference on Robotics and Automation, 2000, pp. 46-54.
Hirzinger G., et al., "On a New Generation of Torque Controlled Light-Weight Robots," Proceedings of the 2001 IEEE, International Conference on Robotics and Automation, 2001, pp. 3356-3363.
Howe R.D., et al., "Robotics for Surgery," Annual Review of Biomedical Engineering, 1999, vol. 1, pp. 211-240.
Interlink Electronics, "Force Sensing Resistors for Medical Equipment, Automotive, and Musical Instruments," 2003, 1 page, Internet: http://www.interlinkelec.com/products/fsr/fsr.htm (last visited Jul. 2003).
International Search Report and Written Opinion for Application No. PCT/US2006/017843, mailed on Jan. 4, 2007, 11 pages.
International Search Report and Written Opinion for Application No. PCT/US2013/043557, mailed on Sep. 6, 2013, 15 pages.
International Search Report and Written Opinion for Application No. PCT/US2013/043564, mailed on Sep. 6, 2013, 16 pages.
International Search Report and Written Opinion for Application No. PCT/US2013/043578, mailed on Sep. 5, 2013, 14 pages.
Kazanzides, Peter et al., "Force Sensing and Control for a Surgical Robot," Int. Conference on Robotics and Automation, May 1992, Nice, France; pp. 612-617, vol. 1, IEEE.
Khatib O., "A Unified Approach for Motion and Force Control of Robot Manipulators: The Operational Space Formulation," IEEE Journa of Robotics and Automation, 1987, vol. Ra-3 (1), pp. 43-52.
Konietschke R., et al., "A Preoperative Planning Procedure for Robotically Assisted Minimally Invasive Interventions," Lecture Notes in Computer Science, CURAC, 2004.
Konietschke R., et al., "Manipulability and Accuracy Measures for a Medical Robot in Minimally Invasive Surgery," Conference Proceeding, In proceeding of: 9th International Symposium on Advances in Robot Kinematics(ARK), Sestri Levante, Italy, Jun. 28-Jul. 1, 2004, 8 pages.

Krupa A., et al., "Towards Semi-Autonomy in Laparoscopic Surgery Through Vision and Force Feedback Control," Experimental Robotics VII, Lecture Notes in Control and Information Sciences, 2001, vol. 271, pp. 189-198.
Maciejewski A.A., et al., "Obstacle Avoidance for Kinematically Redundant Manipulators in Dynamically Varying Environments," International Journal of Robotics Research, 1985, vol. 4 (3), pp. 109-117.
Maciejewski, Anthony A. et al., "The Singular Value Decomposition: Computation and Applications to Robotics," The International Journal of Robotics Research, 1989, pp. 63-79, vol. 8—No. 6, Sage Publications.
Michelin M., et al., "Dynamic Task/Posture Decoupling for Minimally Invasive Surgery Motions," Intelligent Robots and Systems, 2004, vol. 4, pp. 3625-3630.
Monnich, Holger et al., "OP:Sense; Research platform for semi-autonomous robot-assisted surgery with haptic feedback and optical supervision" [online video], 2011 [retrieved on Jun. 12, 2013]. Retrieved from the Internet: <URL: https://www.youtube.com/watch?v=g0ZgSaNtTUw.
Nakamura Y., et al., "Task-Priority Based Redundancy Control of Robot Manipulators," International Journal of Robotics Research, Sage Science Press, Thousand Oaks, US, Jun. 21, 1987, vol. 6 (2), pp. 3-15.
Ortmaier T.J., "Motion Compensation in Minimally Invasive Robotic Surgery," 2002, 5 Chapters, 147 pages.
PCT/US06/17843 International Search Report, mailed Jan. 4, 2007, 6 pages.
PCT/US06/17843 Written Opinion of the International Search Authority, mailed Jan. 4, 2007, 9 pages.
Schreiber G., "Interactive Redundant Robotics: Control of the Inverted Pendulum with Nullspace Motion," Proceedings of the 2001, IEEE/RSJ, International Conference on Intelligent Robots and Systems, 2001, pp. 158-164.
Schreiber G., Steuerung fur Redundante Robotersysteme: Benutzer und Aufgabenorientierte Verwendung Der Redundanz, 2004, 296 pages.
Siciliano B., "Kinematic Control of Redundant Robot Manipulators: A Tutorial," Journal of Intelligent and Robotic Systems, 1990, vol. 3 (3), pp. 201-212.
Siciliano, Bruno et al., "A General Framework for Managing Multiple Tasks in Highly Redundant Robotic Systems," Fifth International Conference of Advanced Robotics, 1991, pp. 1211-1216, IEEE.
Smalley, Eric, "Flexible sensors make robot skin," Technology Research News, Sep. 22-29, 2004, 3 pages, Internet: http://www.trnmag.com/Stories/2004/092204/Flexible_sensors_make_robot_skin%20_092204.html (last visited Dec. 17, 2004).
Stanford University, Dexterous Manipulation Laboratory, "The 'Capaciflector' Proximity Sensor", 2005, 3 pages. Internet: http://www.cdr.stanford.edu/Touch/previous_projects/capaciflector/capaciflector.htm (last visited Jan. 5, 2005).
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Yigit S., et al., "Specific Combined Control Mechanisms for Human Robot Co-Operation," Institute for Process Control and Robotics (IPR), 2003, 6 pages.
Extended European Search Report for Application No. 13798154.4, mailed on Jan. 5, 2016, 9 pages.

* cited by examiner

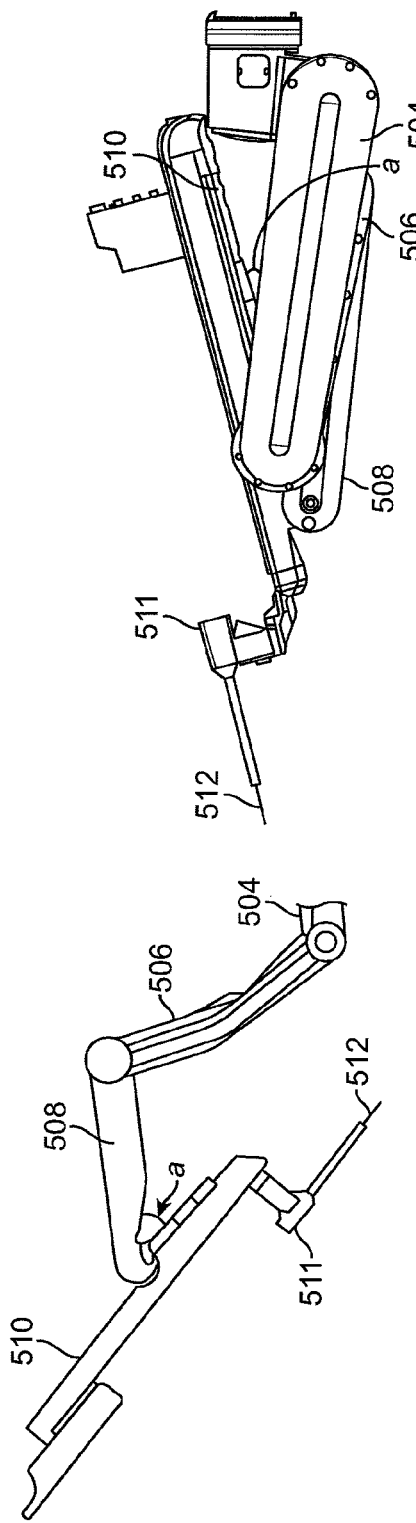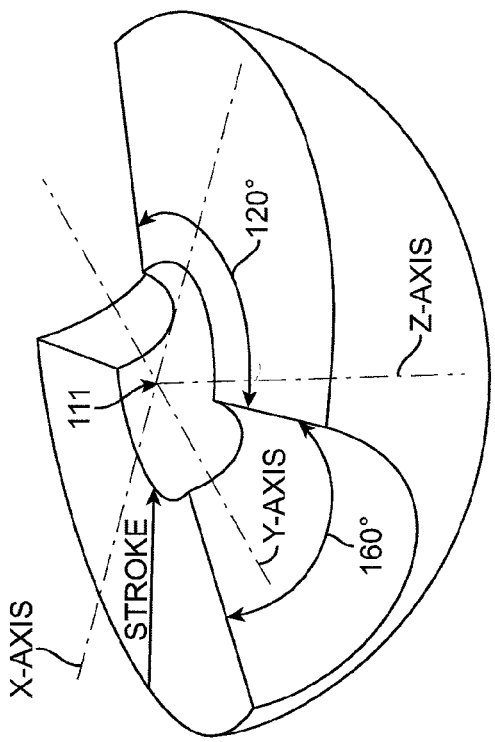
FIG. 6B
FIG. 6C
FIG. 6A

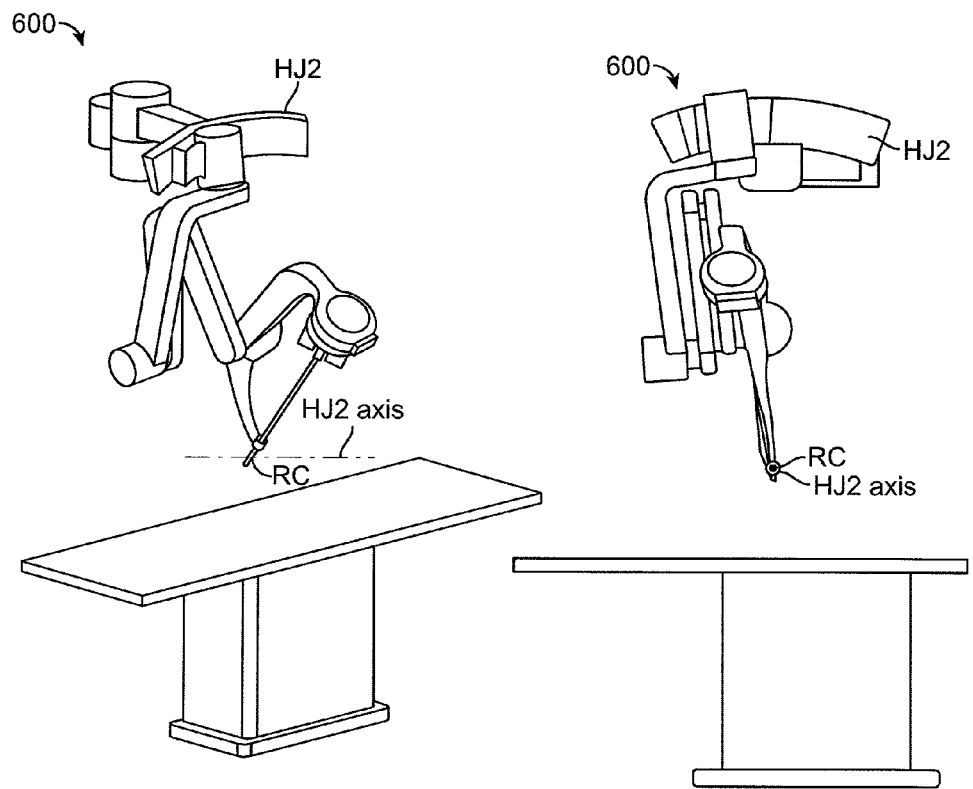
FIG. 13A
FIG. 13B
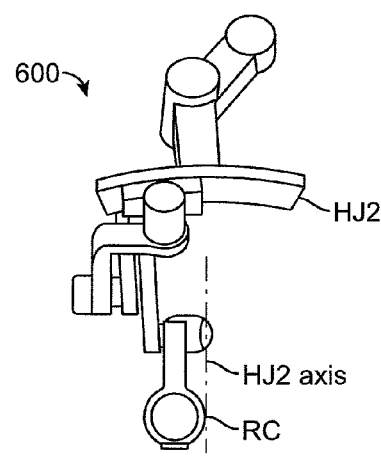
FIG. 13C

SYSTEMS AND METHODS FOR COMMANDED RECONFIGURATION OF A SURGICAL MANIPULATOR USING THE NULL-SPACE

CROSS-REFERENCES TO RELATED APPLICATIONS

This application is a Non-Provisional of and claims the benefit of priority from U.S. Provisional Patent Application No. 61/654,764 filed on Jun. 1, 2012 and entitled "Commanded Reconfiguration of a Surgical Manipulator Using the Null-Space", the full disclosure of which is incorporated herein by reference.

The present application is generally related to the following commonly-owned applications: U.S. application Ser. No. 12/494,695 filed Jun. 30, 2009, entitled "Control of Medical Robotic System Manipulator About Kinematic Singularities;" U.S. application Ser. No. 12/406,004 filed Mar. 17, 2009, entitled "Master Controller Having Redundant Degrees of Freedom and Added Forces to Create Internal Motion;" U.S. application Ser. No. 11/133,423 filed May 19, 2005 (U.S. Pat. No. 8,004,229), entitled "Software Center and Highly Configurable Robotic Systems for Surgery and Other Uses;" U.S. application Ser. No. 10/957,077 filed Sep. 30, 2004 (U.S. Pat. No., 7,594,912), entitled "Offset Remote Center Manipulator For Robotic Surgery;" U.S. application Ser. No. 09/398,507 filed Sep. 17, 1999 (U.S. Pat. No. 6,714,839), entitled "Master Having Redundant Degrees of Freedom;" and U.S. application Ser. Nos. 13/906,713 entitled "Manipulator Arm-to-Patient Collision Avoidance Using a Null-Space;" and Ser. No. 13/906,819 entitled "Systems and Methods for Avoiding Collisions Between Manipulator Arms Using a Null-Space" filed concurrently with the present application; the disclosures of which are incorporated herein by reference in their entireties.

BACKGROUND OF THE INVENTION

The present invention generally provides improved surgical and/or robotic devices, systems, and methods.

Minimally invasive medical techniques are aimed at reducing the amount of tissue which is damaged during diagnostic or surgical procedures, thereby reducing patient recovery time, discomfort, and deleterious side effects. Millions of "open" or traditional surgeries are performed each year in the United States; many of these surgeries can potentially be performed in a minimally invasive manner. However, only a relatively small number of surgeries currently use minimally invasive techniques due to limitations in surgical instruments, and techniques, and the additional surgical training required to master them.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn control the motion of robotic instruments. The robotic surgical instruments can be inserted through small, minimally invasive surgical apertures to treat tissues at surgical sites within the patient, often the trauma associated with accessing for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

The servomechanism used for telesurgery will often accept input from two master controllers (one for each of the surgeon's hands) and may include two or more robotic arms or manipulators. Mapping of the hand movements to the image of the robotic instruments displayed by the image capture device can help provide the surgeon with accurate control over the instruments associated with each hand. In many surgical robotic systems, one or more additional robotic manipulator arms are included for moving an endoscope or other image capture device, additional surgical instruments, or the like.

A variety of structural arrangements can be used to support the surgical instrument at the surgical site during robotic surgery. The driven linkage or "slave" is often called a robotic surgical manipulator, and example linkage arrangements for use as a robotic surgical manipulator during minimally invasive robotic surgery are described in U.S. Pat. Nos. 6,758,843; 6,246,200; and 5,800,423, the full disclosures of which are incorporated herein by reference. These linkages often make use of a parallelogram arrangement to hold an instrument having a shaft. Such a manipulator structure can constrain movement of the instrument so that the instrument shaft pivots about a remote center of spherical rotation positioned in space along the length of the rigid shaft. By aligning this center of rotation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 6,702,805; 6,676,669; 5,855,583; 5,808,665; 5,445,166; and 5,184,601, the full disclosures of which are incorporated herein by reference.

While the new robotic surgical systems and devices have proven highly effective and advantageous, still further improvements would be desirable. For example, when moving the surgical instruments within a minimally invasive surgical site, robotic surgical manipulators may exhibit a significant amount of movement outside the patient, particularly when pivoting instruments about minimally invasive apertures through large angular ranges, which can lead to the moving manipulators inadvertently coming into contact with each other, with instrument carts or other structures in the surgical room, with surgical personnel, and/or with the outer surface of the patient. Alternative manipulator structures have been proposed which employ software control over a highly configurable kinematic manipulator joint set to restrain pivotal motion to the insertion site while inhibiting inadvertent manipulator/manipulator contact outside the patient (or the like). These highly configurable "software center" surgical manipulator systems may provide significant advantages, but may also present challenges. In particular, the mechanically constrained remote-center linkages may have safety advantages in some conditions. Additionally, the wide range of configurations of the numerous joints often included in these manipulators may result in the manipulators being difficult to manually set-up in a configuration that is desirable for a particular procedure. Nonetheless, as the range of surgeries being performed using telesurgical systems continues to expand, there is an increasing demand for expanding the available configurations and the range of motion of the instruments within the patient. Unfortunately, both of these changes can increase the challenges associated with the motion of the manipulators outside the body, and can also increase the importance of avoiding manipulator configurations that are poorly conditioned (such that they unnecessarily limit the dexterity and/or range of motion of the tool inside the surgical workspace).

For these and other reasons, it would be advantageous to provide improved devices, systems, and methods for surgery, robotic surgery, and other robotic applications. It would be particularly beneficial if these improved technologies provided the ability to reconfigure the manipulator arms according to a desired reconfiguration while maintaining a desired end effector state or a desired location of a remote center about which the instrument shaft pivots. Ideally, these improvements would allow a first user to effect movement of an end effector of the manipulator arm during a surgical procedure while allowing a second user to reconfigure the manipulator arms in preparation for and/or during end effector movement. Additionally, it would be desirable to provide such improvements while increasing the range of motion of the instruments for at least some procedures and without significantly increasing the size, mechanical complexity, or costs of these systems, and while maintaining or improving their dexterity.

BRIEF SUMMARY OF THE INVENTION

The present invention generally provides improved robotic and/or surgical devices, systems, and methods. In many embodiments, the invention will employ highly configurable surgical robotic manipulators. These manipulators, for example, may have more degrees of freedom of movement than the associated surgical end effectors have within a surgical workspace. A robotic surgical system in accordance with the present invention typically includes a manipulator arm supporting a robotic surgical instrument and a processor to calculate coordinated joint movements for manipulating an end effector of the instrument. The joints of the robotic manipulators supporting the end effectors allow the manipulator to move throughout a range of different configurations for a given end effector position and/or a given pivot point location. The system allows for reconfiguration of the highly configurable robotic manipulators, in response to a user command, by driving one or more joints of the manipulator according to coordinated movement of the joints calculated by a processor, resulting in the motion of one or more joints of the manipulator within a null-space of the kinematic Jacobian so as to maintain the desired end effector state and/or pivot point location. In various embodiments, a system operator enters a reconfiguration command with a user input device and drives one or more joints of the manipulator within the null-space until the manipulator is reconfigured as desired.

In one aspect of the present invention, a redundant degrees of freedom (RDOF) surgical robotic system with manipulate input is provided. The RDOF surgical robotic system comprises a manipulator assembly, one or more user input devices, and a processor with a controller. A manipulator arm of the assembly has a plurality of joints providing sufficient degrees of freedom that allow a range of joint states for a given end effector state. In response to a received reconfiguration command entered by a user, the system calculates velocities of the plurality of joints within a null-space. The joints are driven according to the reconfiguration command and the calculated movement so as to maintain the desired state of the end effector. In response to receiving a manipulation command to move the end effector with a desired movement, the system calculates end effector displacing movement of the joints by calculating joint velocities within a null-perpendicular-space of the Jacobian orthogonal to the null-space and drives the joints according to the calculated movement to effect the desired end effector movement.

In another aspect of the present invention, the manipulator is configured to move such that an intermediate portion of the instrument shaft pivots about a remote center. Between the manipulator and the instrument, there are a plurality of driven joints providing sufficient degrees of freedom to allow a range of joint states for an end effector position when the intermediate portion of the instrument shaft extends through an access site. A processor having a controller couples the input device to the manipulator. In response to a reconfiguration command, the processor determines movements of one or more joints to effect the desired reconfiguration so that the intermediate portion of the instrument is within the access site during the end effector's desired movement and maintains the desired remote center location about which the shaft pivots. In various embodiments, in response to receiving a manipulation command to effect a desired end effector's movement, the system calculates end effector displacing movement of the joints, which comprises calculating joint velocities within a null-perpendicular-space of the Jacobian orthogonal to the null-space and drives the joints according to the calculated movement to effect the desired end effector movement in which the instrument shaft pivots about the remote center.

In certain embodiments, the end effector displacing movement of the joints is calculated so as to avoid driving a first set of joints of the plurality such that either the first set of joints are effectively locked out, or so that the first set of joints are not driven to effect the end effector displacing movement. The first set of joints may include one or more joints of the manipulator arm. The reconfiguration movements of the joints, however, may be calculated so as to drive the first set of joints of the plurality to effect the desired end effector movement. The reconfiguration movement of the first set of joints may also be calculated so that the movement of a joint from the first set of joints provides a substantially constant speed of the joint for a duration of the reconfiguration. In some embodiments, a joint from the first set of joints of the manipulator is a revolute joint coupling the manipulator arm to the base. The desired state of the end effector may include a desired position, velocity or acceleration of the end effector. Generally, the manipulation command and the reconfiguration command are separate inputs, typically being received from separate users on separate input device, or these separate inputs may be received from the same user. In some embodiments, the end effector manipulation command is received from an input device by a first user, such as a surgeon entering the command on a surgical console master input, while the reconfiguration command is received from an input device by a second user on a separate input device, such as a physician's assistant entering the reconfiguration command on a patient side cart input device. In other embodiments, the end effector manipulation command and the reconfiguration command are both received by the same user from input devices at a surgical console. In other embodiments, the end effector manipulation command and the reconfiguration command are both received by the same user from input devices at a patient side cart.

In one aspect, the proximal portion of the manipulator arm is attached to the base such that movement of the proximal portion relative to the base is inhibited while the joints are driven. The proximal portion may be coupled to the base by a joint such that the proximal portion of the manipulator arm is moveable relative to the base while the joints are driven. In an example embodiment, the joint coupling the proximal portion of the manipulator to the base by a revolute joint that supports the manipulator arm such that joint movement of the revolute joint pivots one or more joints of the manipulator arm about a pivotal axis of the revolute joints. In certain embodiments, the pivotal axis of the revolute joint extends from the joints through a remote center about which an instrument shaft of the end effector pivots. In one aspect, movement of the revolute joint pivots one or more joints of the manipulator arm about a cone distally tapered and oriented towards the distal end effector, typically the remote center. The cone around which the manipulator arm pivots in this aspect, corresponds to a cone shaped void within the range of motion of the tool tip, in which the movement of the tool may be impossible or impaired, discussed in further detail below.

In another aspect, the joint coupling the proximal portion of the manipulator to the base is moveable relative to the base along a path, typically an arcuate or substantially circular path such that movement of the joint along the path pivots one or more joints of the manipulator arm about an axis extending through a distal portion of the manipulator arm near the instrument, preferably through a remote center about which the instrument shaft pivots. In some embodiments, the manipulator includes a revolute joint coupling the proximal portion of the manipulator to the base, the revolute joint being moveable relative to the base along a path, which may linear, arcuate or substantially circular.

In yet another aspect of the present invention, a surgical robotic manipulator with a proximal revolute joint and a distal parallelogram linkage is provided, the pivotal axis of the revolute joint substantially intersecting with the axis of the instrument shaft of the end effector, preferably at a remote center if applicable. The system further includes a processor having a controller coupling the input to the manipulator arm and configured to calculate a movement of the plurality of joints in response to the reconfiguration command so that the calculated velocities of the joints are within a null-space of the Jacobian. The system includes an input device for receiving a reconfiguration command to move a first set of joints of the plurality of joints with a desired reconfiguration movement while the end effector is in the desired state.

A further understanding of the nature and advantages of the present invention will become apparent by reference to the remaining portions of the specification and drawings.

BRIEF DESCRIPTION OF THE DRAWINGS

FIGS. 6A-6B show an example manipulator arm in the pitch forward configuration and pitch back configurations, respectively.

FIG. 6C shows a graphical representation of the range of motion of the surgical instrument tool tip of an example manipulator arm, including a cone of silence or conical tool access limit zone in each of the pitch forward and pitch back configurations.

FIGS. 12A-12D and 13A-13C show example manipulator arms having a proximal joint that translates a proximal joint supporting the manipulator arm about a path of the joint.

DETAILED DESCRIPTION OF THE INVENTION

Figure 1A:
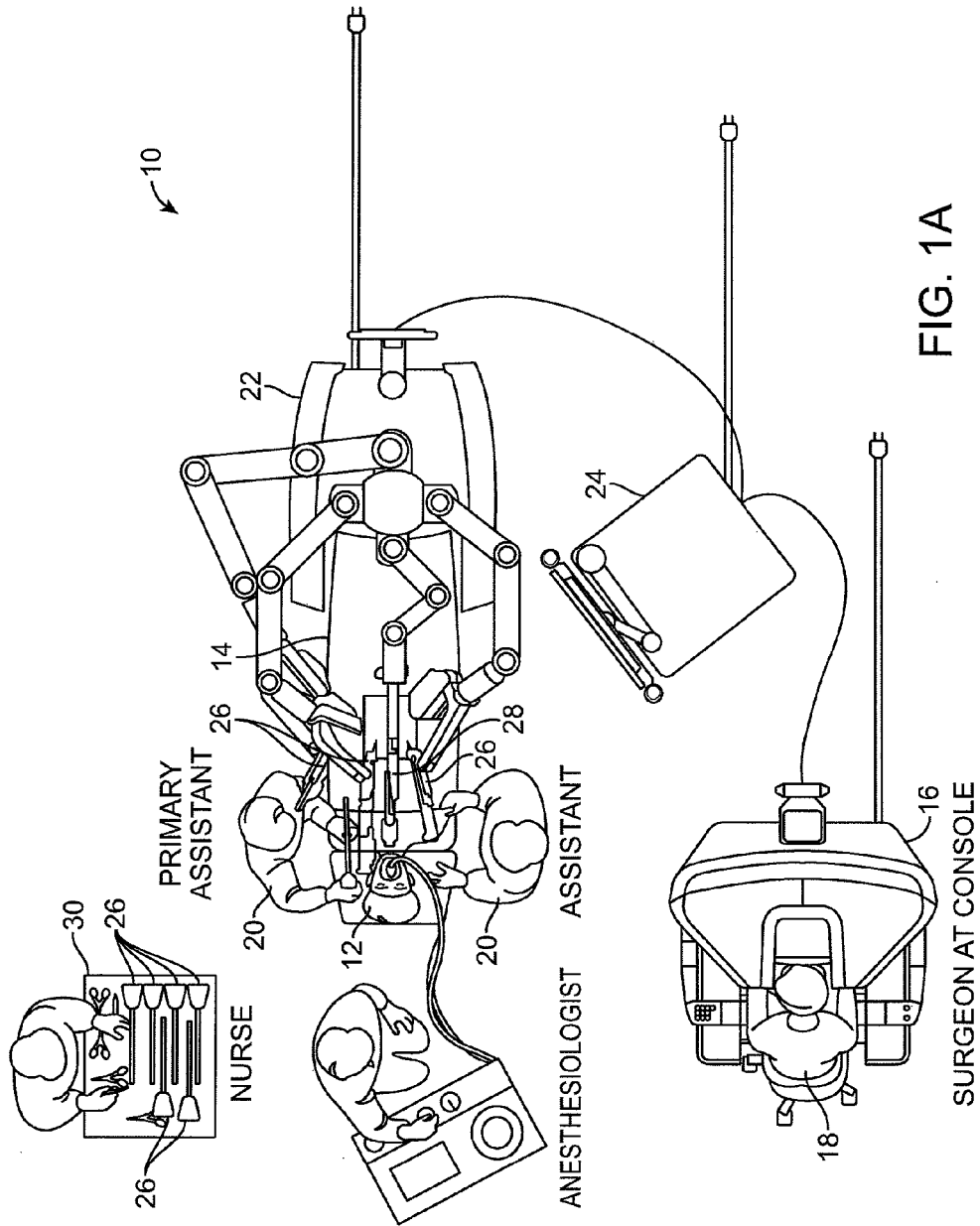
FIG. 1A is an overhead view of a robotic surgical system in accordance with embodiments of the present invention, the robotic surgical system having a surgical station with a plurality of robotic manipulators for robotically moving surgical instruments having surgical end effectors at an internal surgical site within a patient.

The present invention generally provides improved surgical and robotic devices, systems, and methods. The invention is particularly advantageous for use with surgical robotic systems in which a plurality of surgical tools or instruments will be mounted on and moved by an associated plurality of robotic manipulators during a surgical procedure. The robotic systems will often comprise telerobotic, telesurgical, and/or telepresence systems that include processors configured as master-slave controllers. By providing robotic systems employing processors appropriately configured to move manipulator assemblies with articulated linkages having relatively large numbers of degrees of freedom, the motion of the linkages can be tailored for work through a minimally invasive access site. The large number of degrees of freedom allows a system operator, or an assistant, to reconfigure the linkages of the manipulator assemblies while maintaining the desired end effector state, optionally in preparation for surgery and/or while another use maneuvers the end effector during a surgical procedure.

The robotic manipulator assemblies described herein will often include a robotic manipulator and a tool mounted thereon (the tool often comprising a surgical instrument in surgical versions), although the term "robotic assembly" will also encompass the manipulator without the tool mounted thereon. The term "tool" encompasses both general or industrial robotic tools and specialized robotic surgical instruments, with these later structures often including an end effector that is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base which is fixed in space during at least a portion of a robotic procedure, and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

The end effector will typically move in the workspace with between two and six degrees of freedom. As used herein, the term "position" encompasses both location and orientation. Hence, a change in a position of an end effector (for example) may involve a translation of the end effector from a first location to a second location, a rotation of the end effector from a first orientation to a second orientation, or a combination of both. When used for minimally invasive robotic surgery, movement of the manipulator assembly may be controlled by a processor of the system so that a shaft or intermediate portion of the tool or instrument is constrained to a safe motion through a minimally invasive surgical access site or other aperture. Such motion may include, for example, axial insertion of the shaft through the aperture site into a surgical workspace, rotation of the shaft about its axis, and pivotal motion of the shaft about a pivot point adjacent the access site.

Many of the example manipulator assemblies described herein have more degrees of freedom than are needed to position and move an end effector within a surgical site. For example, a surgical end effector that can be positioned with six degrees of freedom at an internal surgical site through a minimally invasive aperture may in some embodiments have nine degrees of freedom (six end effector degrees of freedom—three for location, and three for orientation—plus three degrees of freedom to comply with the access site constraints), but may have ten or more degrees of freedom. Highly configurable manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly within the null-space of the Jacobian.

The invention provides robotic linkage structures which are particularly well suited for surgical (and other) applications in which a wide range of motion is desired, and for which a limited dedicated volume is available due to the presence of other robotic linkages, surgical personnel and equipment, and the like. The large range of motion and reduced volume needed for each robotic linkage may also provide greater flexibility between the location of the robotic support structure and the surgical or other workspace, thereby facilitating and speeding up setup.

The term "state" of a joint or the like will often herein refer to the control variables associated with the joint. For example, the state of an angular joint can refer to the angle defined by that joint within its range of motion, and/or to the angular velocity of the joint. Similarly, the state of an axial or prismatic joint may refer to the joint's axial position, and/or to its axial velocity. While many of the controllers described herein comprise velocity controllers, they often also have some position control aspects. Alternative embodiments may rely primarily or entirely on position controllers, acceleration controllers, or the like. Many aspects of control system that can be used in such devices are more fully described in U.S. Pat. No. 6,699,177, the full disclosure of which is incorporated herein by reference. Hence, so long as the movements described are based on the associated calculations, the calculations of movements of the joints and movements of an end effector described herein may by performed using a position control algorithm, a velocity control algorithm, a combination of both, and/or the like.

In certain embodiments, the tool of an example manipulator arm pivots about a pivot point adjacent a minimally invasive aperture. The system may utilize a hardware remote center, such as the remote center kinematics described in U.S. Pat. No. 6,786,896, the contents of which are incorporated herein in their entirety. Such systems may utilize a double parallelogram linkage which constrains movement of the linkages such that the shaft of the instrument supported by the manipulator pivots about a remote center point. Alternative mechanically constrained remote center linkage systems are known and/or may be developed in the future. Surprisingly, work in connection with the present invention indicates that remote center linkage systems may benefit from highly configurable kinematic architectures. In particular when a surgical robotic system has a linkage that allows pivotal motion about two axes intersecting at or near a minimally invasive surgical access site, the spherical pivotal motion may encompass the full extent of a desired range of motion within the patient, but may still suffer from avoidable deficiencies (such as being poorly conditioned, being susceptible to arm-to-arm or arm-to-patient contact outside the patient, and/or the like). At first, adding one or more additional degrees of freedom that are also mechanically constrained to pivotal motion at or near the access site may appear to offer few or any improvements in the range of motion. Nonetheless, such joints can provide significant advantages by allowing the overall system to be configured in or driven toward a collision-inhibiting pose, by further extending the range of motion for other surgical procedures, and the like. In some embodiments, the system may utilize software to achieve a remote center, such as described in U.S. Pat. No. 8,004,229, the entire contents of which are incorporated herein by reference. In a system having a software remote center, the processor calculates movement of the joints so as to pivot an intermediate portion of the instrument shaft about a pivot point determined, as opposed to a mechanical constraint. By having the capability to compute software pivot points, different modes characterized by the compliance or stiffness of the system can be selectively implemented. More particularly, different system modes over a range of pivot points/centers (e.g., moveable pivot points, passive pivot points, fixed/rigid pivot point, soft pivot points) can be implemented as desired.

Despite the many advantages of a robotic surgical system having multiple highly configurable manipulators, since the manipulators include a relatively large number of joints and links between the base and instrument, manual positioning of the links can be challenging and complicated. Even when the manipulator structure is balanced so as to avoid gravitational effects, attempting to align each of the joints in an appropriate arrangement or to reconfigure the manipulator as desired can be difficult, time consuming, and may involve significant training and/or skill. The challenges can be even greater when the links of the manipulator are not balanced about the joints, such that positioning such a highly configurable structures in an appropriate configuration before or during surgery can be a struggle due to the manipulator arm length and the passive and limp design in many surgical systems. The present invention allows a user, such as a physician's assistant, to quickly and easily reconfigure the manipulator arm, while maintaining the desired end effector state, optionally even during movement of the end effector during a surgical procedure. In some embodiments, the manipulation and reconfiguration input can come from the same person (e.g. a user at the surgeon's console or the patient side cart).

Embodiments of the invention may include a user input that is configured to take advantage of the degrees of freedom of a manipulator structure. Rather than manually reconfiguring the manipulator, the input facilitates use of driven joints of the kinematic linkage to reconfigure the manipulator structure in response to entry of a reconfiguration command by a user. In certain embodiments, the user input for receiving the reconfiguration command is incorporated into and/or disposed near the manipulator arm. The input may comprise a centralized input device to facilitate reconfiguration of one or more joints, such as a cluster of buttons on the patient side cart or a joystick. Typically, the input device for receiving the reconfiguration command is separate from the input for receiving a manipulation command to effect movement of the end effector. A controller of the surgical system may include a processor with readable memory having joint controller programming instructions or code recorded thereon that allows the processor to derive suitable joint commands for driving the joints recorded thereon so as to allow the controller to effect the desired reconfiguration in response to entry of the reconfiguration command.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Referring now to the drawings, in which like reference numerals represent like parts throughout the several views, FIG. 1A is an overhead view illustration of a Minimally Invasive Robotic Surgical (MIRS) system 10, in accordance with many embodiments, for use in performing a minimally invasive diagnostic or surgical procedure on a Patient 12 who is lying down on an Operating table 14. The system can include a Surgeon's Console 16 for use by a surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the surgeon 18 views the surgical site through the Console 16. An image of the surgical site can be obtained by an endoscope 28, such as a stereoscopic endoscope, which can be manipulated by the Patient Side. Cart 22 so as to orient the endoscope 28. The Electronics Cart 24 can be used to process the images of the surgical site for subsequent display to the surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 1B:
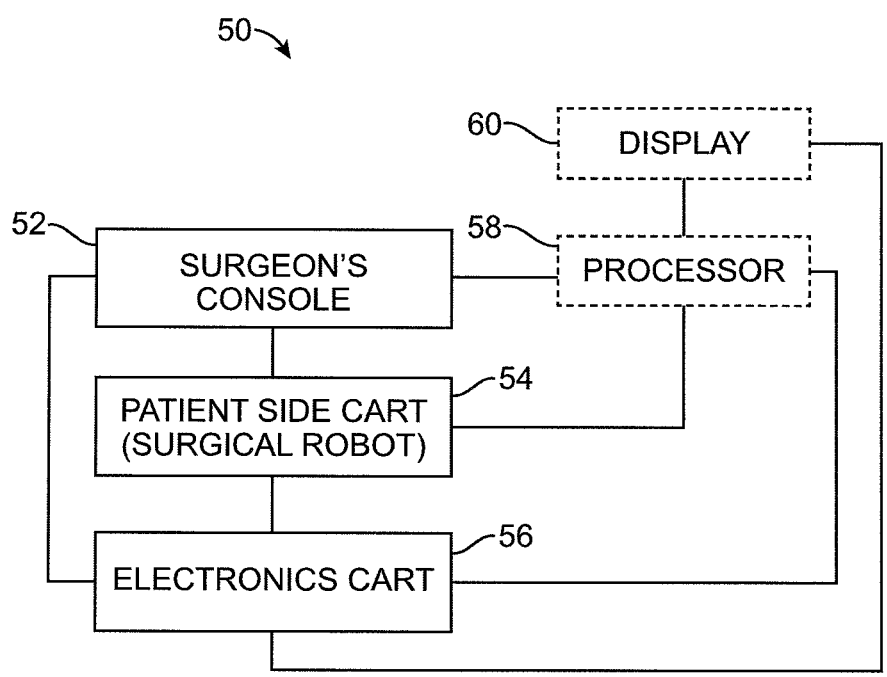
FIG. 1B diagrammatically illustrates the robotic surgical system of FIG. 1A.

FIG. 1B diagrammatically illustrates a robotic surgery system 50 (such as MIRS system 10 of FIG. 1A). As discussed above, a Surgeon's Console 52 (such as Surgeon's Console 16 in FIG. 1A) can be used by a surgeon to control a Patient Side Cart (Surgical Robot) 54 (such as Patent Side Cart 22 in FIG. 1A) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1A). As discussed above, the Electronics Cart 56 can process the captured images in a variety of ways prior to any subsequent display. For example, the Electronics Cart 56 can overlay the captured images with a virtual control interface prior to displaying the combined images to the surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together so as to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 2:
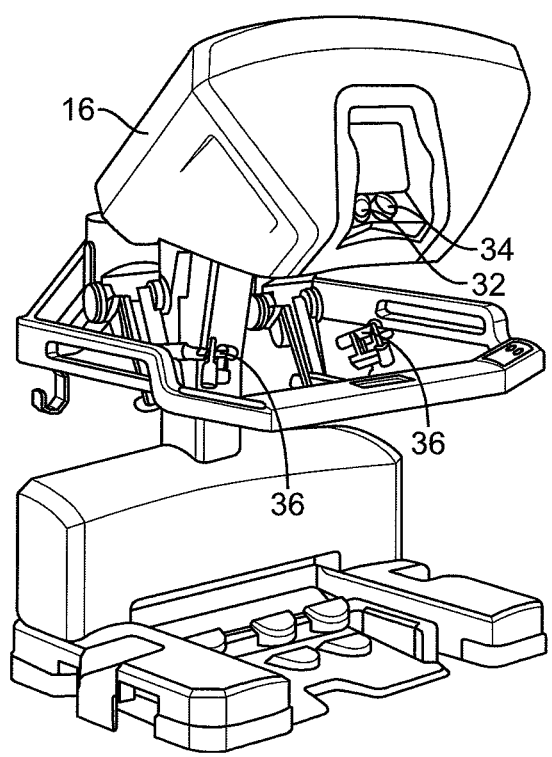
FIG. 2 is a perspective view illustrating a master surgeon console or workstation for inputting surgical procedure commands in the surgical system of FIG. 1A, the console including a processor for generating manipulator command signals in response to the input commands.

FIG. 2 is a perspective view of the Surgeon's Console 16. The Surgeon's Console 16 includes a left eye display 32 and a right eye display 34 for presenting the surgeon 18 with a coordinated stereo view of the surgical site that enables depth perception. The Console 16 further includes one or more input control devices 36, which in turn cause the Patient Side Cart 22 (shown in FIG. 1A) to manipulate one or more tools. The input control devices 36 can provide the same degrees of freedom as their associated tools 26 (shown in FIG. 1A) so as to provide the surgeon with telepresence, or the perception that the input control devices 36 are integral with the tools 26 so that the surgeon has a strong sense of directly controlling the tools 26. To this end, position, force, and tactile feedback sensors (not shown) may be employed to transmit position, force, and tactile sensations from the tools 26 back to the surgeon's hands through the input control devices 36.

The Surgeon's Console 16 is usually located in the same room as the patient so that the surgeon may directly monitor the procedure, be physically present if necessary, and speak to an Assistant directly rather than over the telephone or other communication medium. However, the surgeon can be located in a different room, a completely different building, or other remote location from the Patient allowing for remote surgical procedures.

Figure 3:
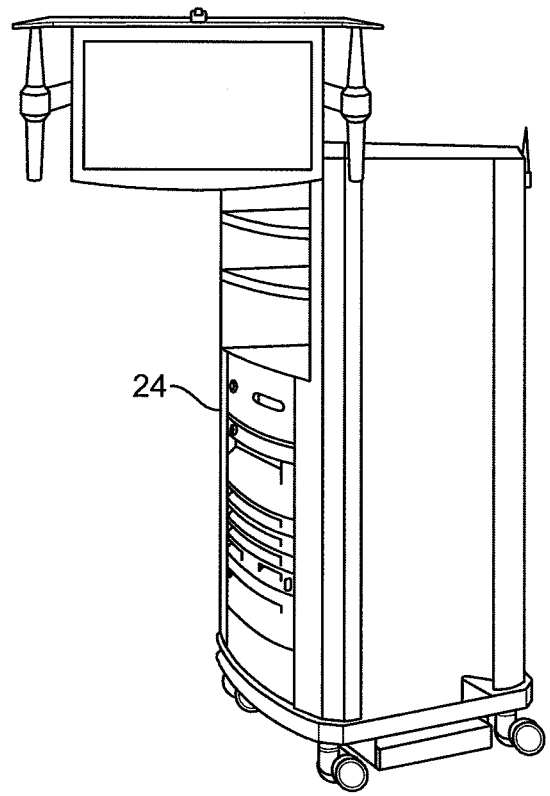
FIG. 3 is a perspective view of the electronics cart of FIG. 1A.

FIG. 3 is a perspective view of the Electronics Cart 24. The Electronics Cart 24 can be coupled with the endoscope 28 and can include a processor to process captured images for subsequent display, such as to a surgeon on the Surgeon's Console, or on another suitable display located locally and/or remotely. For example, where a stereoscopic endoscope is used, the Electronics Cart 24 can process the captured images so as to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations.

Figure 4:
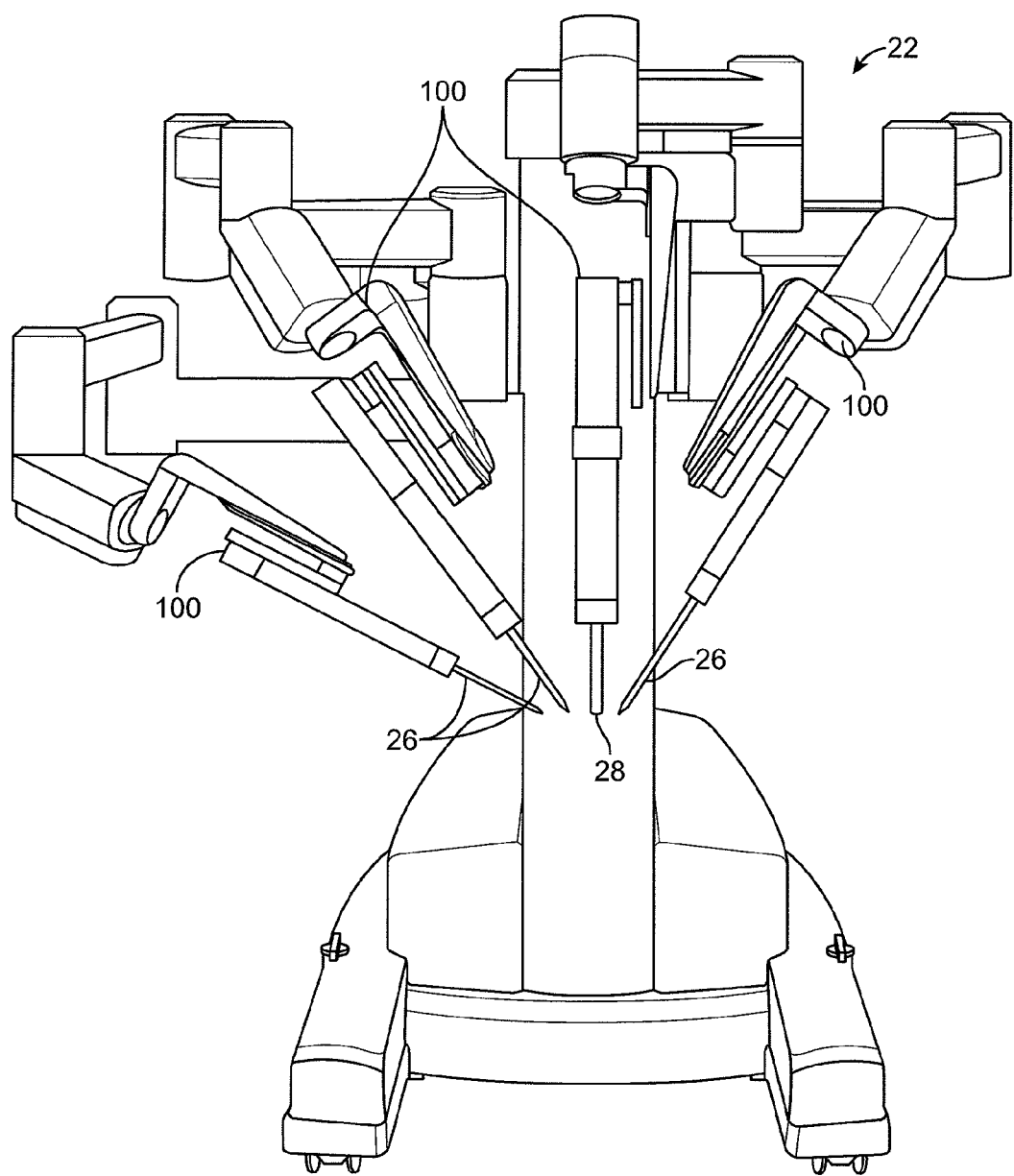
FIG. 4 is a perspective view of a patient side cart having four manipulator arms.

FIG. 4 shows a Patient Side Cart 22 having a plurality of manipulator arms, each supporting a surgical instrument or tool 26 at a distal end of the manipulator arm. The Patient Side Cart 22 shown includes four manipulator arms 100 which can be used to support either a surgical tool 26 or an imaging device 28, such as a stereoscopic endoscope used for the capture of images of the site of the procedure. Manipulation is provided by the robotic manipulator arms 100 having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical instruments or tools 26 when they are positioned within the field-of-view of the imaging device 28.

Regarding surgical tool 26, a variety of alternative robotic surgical tools or instruments of different types and differing end effectors may be used, with the instruments of at least some of the manipulators being removed and replaced during a surgical procedure. Several of these end effectors, including DeBakey Forceps, microforceps, Potts scissors, and clip applier include first and second end effector elements which pivot relative to each other so as to define a pair of end effector jaws. Other end effectors, including scalpel and electrocautery probe have a single end effector element. For instruments having end effector jaws, the jaws will often be actuated by squeezing the grip members of handle. Single end effector instruments may also be actuated by gripping of the grip members, for example, so as to energize an electrocautery probe.

The elongate shaft of instrument 26 allow the end effectors and the distal end of the shaft to be inserted distally into a surgical worksite through a minimally invasive aperture, often through an abdominal wall or the like. The surgical worksite may be insufflated, and movement of the end effectors within the patient will often be effected, at least in part, by pivoting of the instrument 26 about the location at which the shaft passes through the minimally invasive aperture. In other words, manipulators 100 will move the proximal housing of the instrument outside the patient so that shaft extends through a minimally invasive aperture location so as to help provide a desired movement of end effector. Hence, manipulators 100 will often undergo significant movement outside patient P during a surgical procedure.

Exemplary manipulator arms in accordance with many embodiments of the present invention can be understood with reference to FIGS. 5A-13C. As described above, a manipulator arm generally supports a distal instrument or surgical tool and effects movements of the instrument relative to a base. As a number of different instruments having differing end effectors may be sequentially mounted on each manipulator during a surgical procedure (typically with the help of a surgical assistant), a distal instrument holder will preferably allow rapid removal and replacement of the mounted instrument or tool. As can be understood with reference to FIG. 4, manipulators are proximally mounted to a base of the patient side cart. Typically, the manipulator arm includes a plurality of linkages and associated joints extending between the base and the distal instrument holder. In one aspect, an example manipulator includes a plurality of joints having redundant degrees of freedom such that the joints of the manipulator arm can be driven into a range of differing configurations for a given end effector position. This may be the case for any of the embodiments of manipulator arms disclosed herein.

Figure 5A:
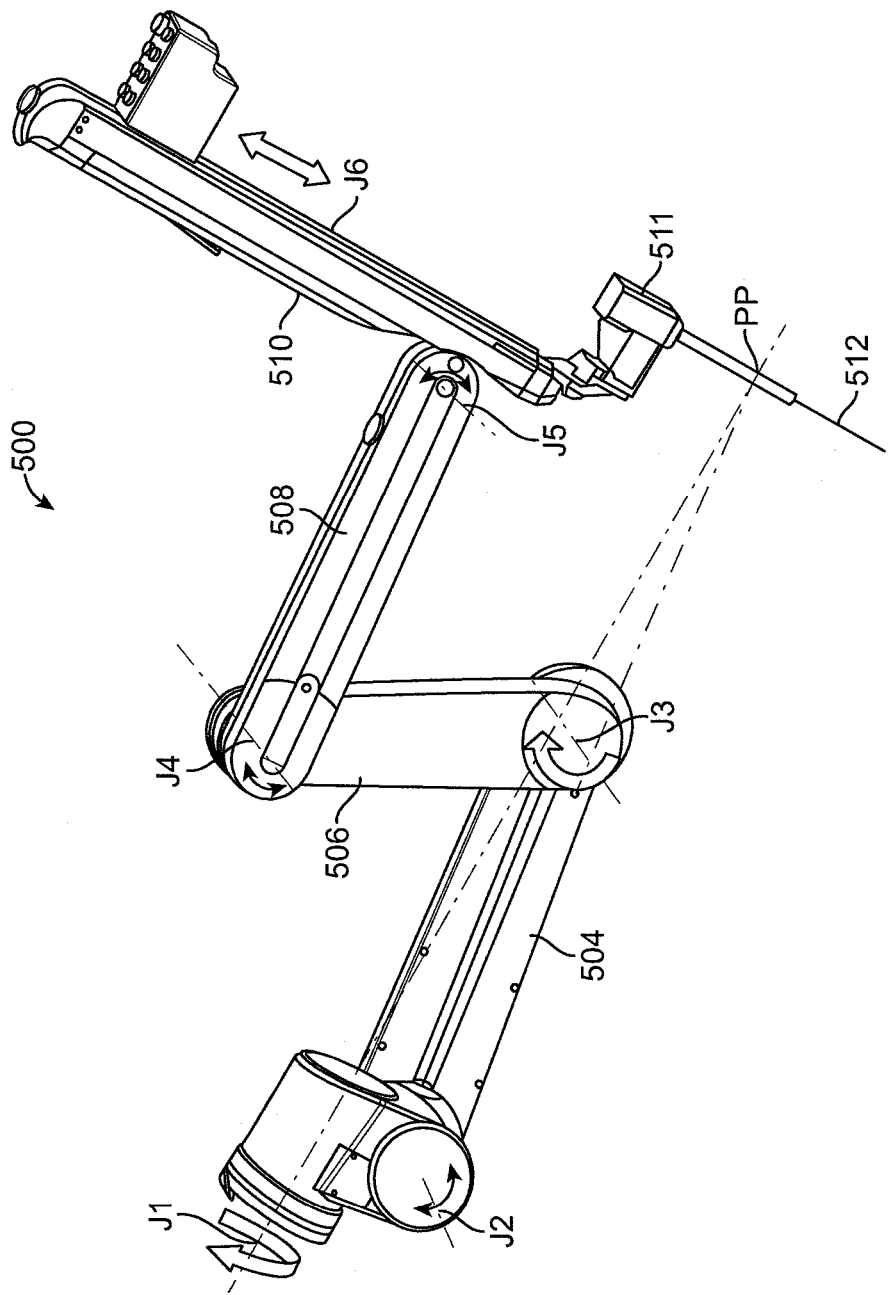
FIGS. 5A-5D show an example manipulator arm.

In certain embodiments, such as shown for example in FIG. 5A, an example manipulator arm includes a proximal revolute joint J1 that rotates about a first joint axis so as to revolve the manipulator arm distal of the joint about the joint axis. In some embodiments, revolute joint J1 is mounted directly to the base, while in other embodiments, joint J1 may be mounted to one or more movable linkages or joints. The joints of the manipulator, in combination, have redundant degrees of freedom such that the joints of the manipulator arm can be driven into a range of differing configurations for a given end effector position. For example, the manipulator arm of FIGS. 5A-5D may be maneuvered into differing configurations while the distal member 511 (such as a cannula through which the tool 512 or instrument shaft extends) supported within the instrument holder 510 maintains a particular state and may include a given position or velocity of the end effector. Distal member 511 is typically a cannula through which the tool shaft 512 extends, and the instrument holder 510 is typically a carriage (shown as a brick-like structure that translates on a spar) to which the instrument attaches before extending through the cannula 511 into the body of the patient through the minimally invasive aperture.

Figure 5B:
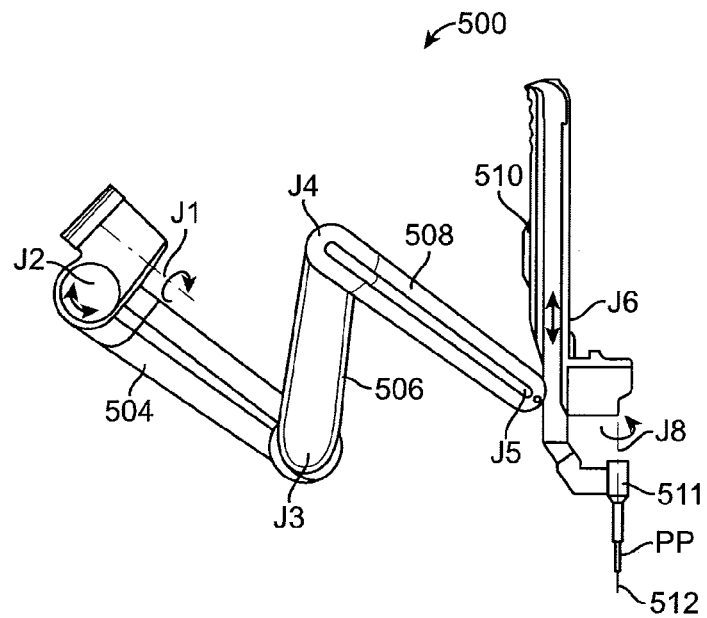
Figure 5D:
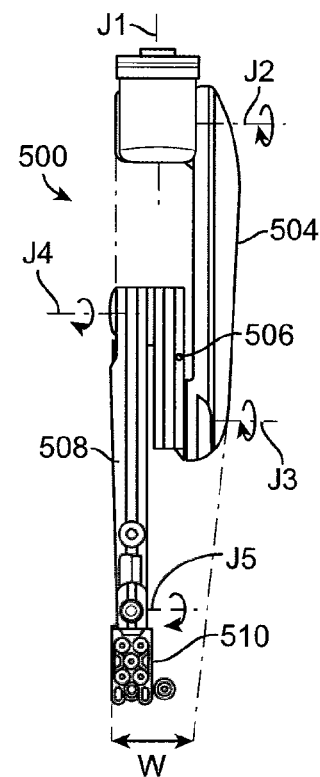
Figure 5C:
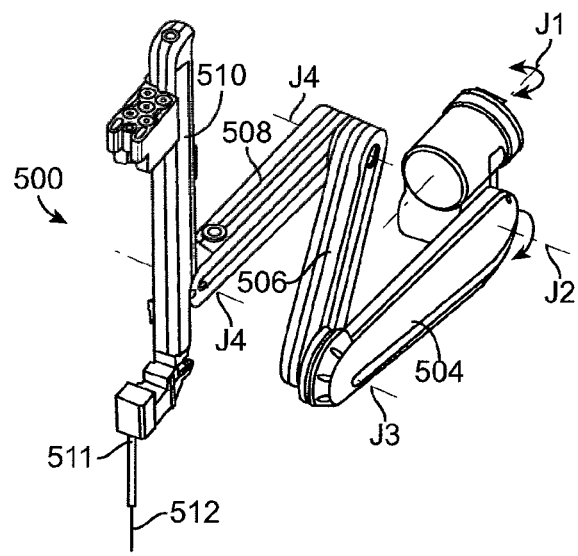

Describing the individual links of manipulator arm 500 of FIGS. 5A-5D along with the axes of rotation of the joints connecting the links as illustrated in FIG. 5A-5D, a first link 504 extends distally from a pivotal joint J2 which pivots about its joint axis and is coupled to revolute joint J1 which rotates about its joint axis. Many of the remainder of the joints can be identified by their associated rotational axes, as shown in FIG. 5A. For example, a distal end of first link 504 is coupled to a proximal end of a second link 506 at a pivotal joint J3 that pivots about its pivotal axis, and a proximal end of a third link 508 is coupled to the distal end of the second link 506 at a pivotal joint J4 that pivots about its axis, as shown. The distal end of the third link 508 is coupled to instrument holder 510 at pivotal joint J5. Typically, the pivotal axes of each of joints J2, J3, J4, and J5 are substantially parallel and the linkages appear "stacked" when positioned next to one another, as shown in FIG. 5D, so as to provide a reduced width w of the manipulator arm and improve patient clearance during maneuvering of the manipulator assembly. In certain embodiments, the instrument holder also includes additional joints, such as a prismatic joint J6 that facilitates axial movement of instrument 306 through the minimally invasive aperture and facilitates attachment of the instrument holder to a cannula through which the instrument is slidably inserted.

The distal member or cannula 511 through which the tool 512 extends may include additional degrees of freedom distal of instrument holder 510. Actuation of the degrees of freedom of the instrument will often be driven by motors of the manipulator, and alternative embodiments may separate the instrument from the supporting manipulator structure at a quickly detachable instrument holder/instrument interface so that one or more joints shown here as being on the instrument are instead on the interface, or vice versa. In some embodiments, cannula 511 includes a rotational joint J7 (not shown) near or proximal of the insertion point of the tool tip or the pivot point PP, which generally is disposed at the site of a minimally invasive aperture. A distal wrist of the instrument allows pivotal motion of an end effector of surgical tool 512 about instrument joints axes of one or more joints at the instrument wrist. An angle between end effector jaw elements may be controlled independently of the end effector location and orientation.

The range of motion of an example manipulator assembly can be appreciated by referring to FIGS. 6A-6C. During a surgical procedure, an example manipulator arm can be maneuvered into a pitch forward configuration, as shown in FIG. 6A, or into a pitch back configuration, as shown in FIG. 6B, as needed to access particular patient tissues within a surgical workspace. A typical manipulator assembly includes an end effector that can pitch forwards and backwards about an axis by at least ±60 degrees, preferably by about ±75 degrees, and can also yaw about an axis by ±80 degrees. Although this aspect allows for increased maneuverability of the end effector with the assembly, there may be configurations in which movement of the end effector may be limited, particularly when the manipulator arm is in the full pitch forward or full pitch back configuration as in FIGS. 6A and 6B. In one embodiment, the manipulator arm has a Range of Motion (ROM) of (+/−75 deg) for the outer pitch, and (+/−300 deg) for the outer yaw joints, respectively. In some embodiments, the ROM may be increased for the outer pitch to provide a ROM larger than (+/−90 deg) in which case the "cone of silence" could be made to disappear entirely, although generally the inner sphere associated with insertion limitations would remain. It is appreciated that various embodiments may be configured to have increased or decreased ROM, that the above noted ROMs are provided for illustrative purposed, and further that the invention is not limited to the ROMs described herein.

FIG. 6C graphically represents the overall range of motion and workspace of the tool tip of the example manipulator of FIGS. 5A-5B. Although the workspace is shown as hemisphere, it may also be represented as a sphere depending on the range of motion and configuration of one or more revolute joints of the manipulator, such as joint J1. As shown, the hemisphere in FIG. 6C includes a central, small spherical void as well as two conical voids. The voids represent the areas in which movement of the tool tip may be impossible due to mechanical constraints or unfeasible due to extremely high joint velocities that make movement of the end effector difficult or slow. For these reasons, the conical void are referred to as the "cone of silence." In some embodiments, the manipulator arm may reach a singularity at a point within the cone. Since movement of the manipulator within or near the cone of silence may be impaired, it can be difficult to move the manipulator arm away from the cone of silence without manually moving one or more links of the manipulator to reconfigure the linkages and joints of the manipulator, which often requires an alternative operating mode and delays the surgical procedure.

Movement of the instrument shaft into or near these conical portions typically occurs when the angle between distal linkages in the manipulator is relatively small. Such configurations can be avoided by reconfiguring the manipulator to increase the angles between linkages (so that the linkages are moved into a more orthogonal position relative to each other). For example, in the configurations shown in FIGS. 6A and 6B, when the angle between the distal most link and the instrument holder (angle a) becomes relatively small movement of the manipulator may become more difficult. Depending on the range of joint movements in the remaining joints in various embodiments, when the angle between certain linkages decreases, movement of the manipulator may be inhibited and in some cases, the manipulator arm may no longer be redundant. A manipulator configuration in which the instrument shaft nears these conical portions, or in which the angles between linkages are relatively low is said to be "poorly conditioned" such that maneuverability and dexterity of the manipulator arm is limited. It is desirable that the manipulator be "well-conditioned" so as to maintain dexterity and range of movement. In one aspect, the present invention allows a user to avoid movement of the instrument shaft near the above described conical portions by simply entering a command to reconfigure the manipulator as desired, even during movement of the end effector in a surgical procedure. This aspect is particularly useful should the manipulator, for whatever reason, become "poorly conditioned."

While the embodiments of the manipulator described above may be utilized in the present invention, some embodiments may include additional joints, which may also be used to improve dexterity and the conditioning of the manipulator arm. For example, an example manipulator may include a revolute joint and/or linkage proximal of joint J1 which can be used to revolve the manipulator arm of FIG. 5A, and its associated cone of silence, about, an axis of the revolute joint so as to reduce or eliminate the cone of silence. In another embodiment, the example manipulator may also include a distal pivotal joint that pivots the instrument holder about an axis substantially perpendicular to joint J5, thereby offsetting the tool tip so as to further reduce the cone of silence and improve the range of movement of the surgical tool. In still another embodiment, a proximal joint of the manipulator arm, such as J1, may be movably mounted on the base, so as to move or shift the cone of silence as needed and improve the range of motion of the manipulator tool tip. The use and advantages of such additional joints can be understood by referring to FIGS. 7A-13C, which illustrate examples of such joints, which may each be used independent of one another or used in combination, in any of the example manipulator arms described herein.

Figure 7A:
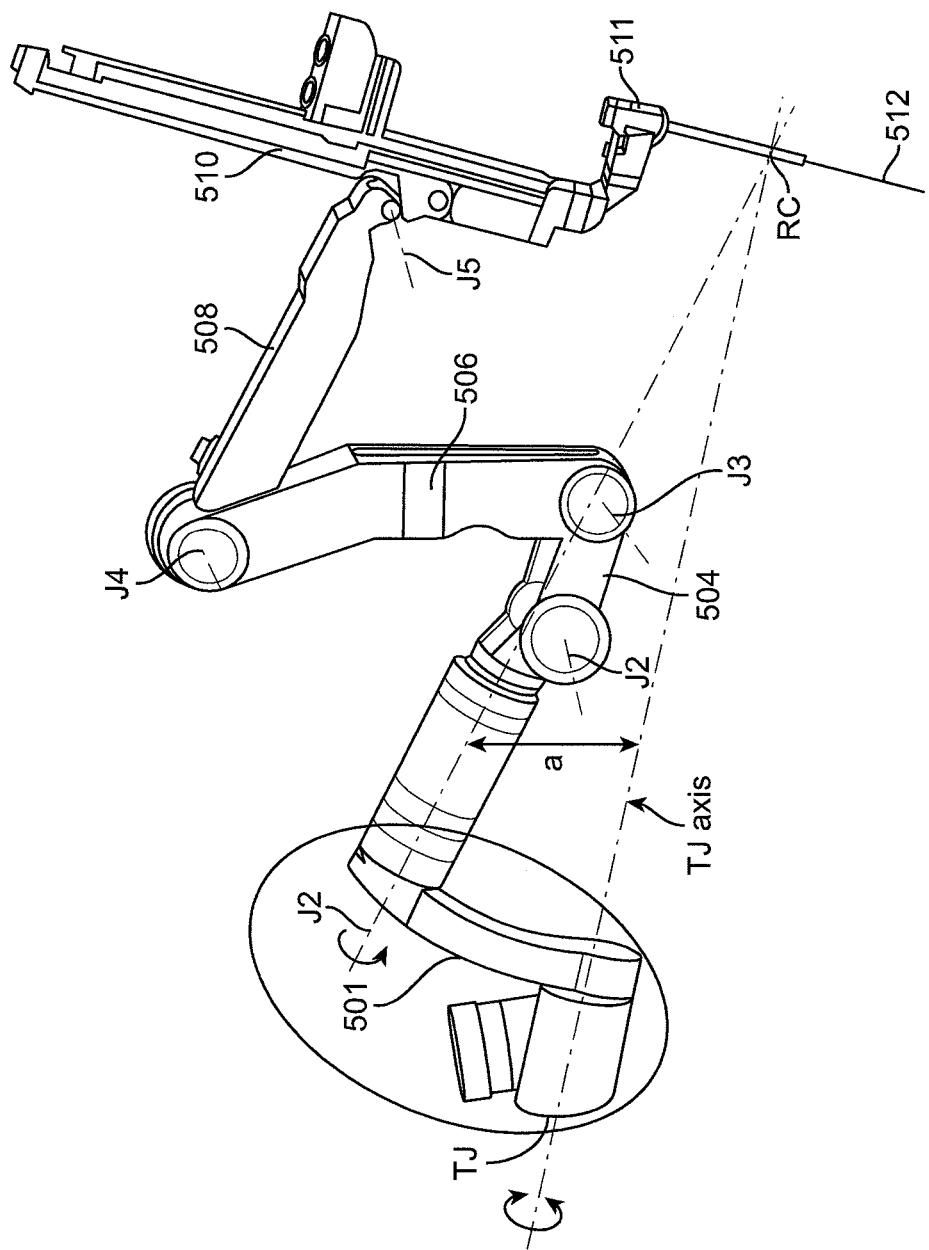
FIG. 7A shows example manipulator arms having a proximal revolute joint that revolves the manipulator arm about an axis of a proximal revolute joint.
Figure 7B:
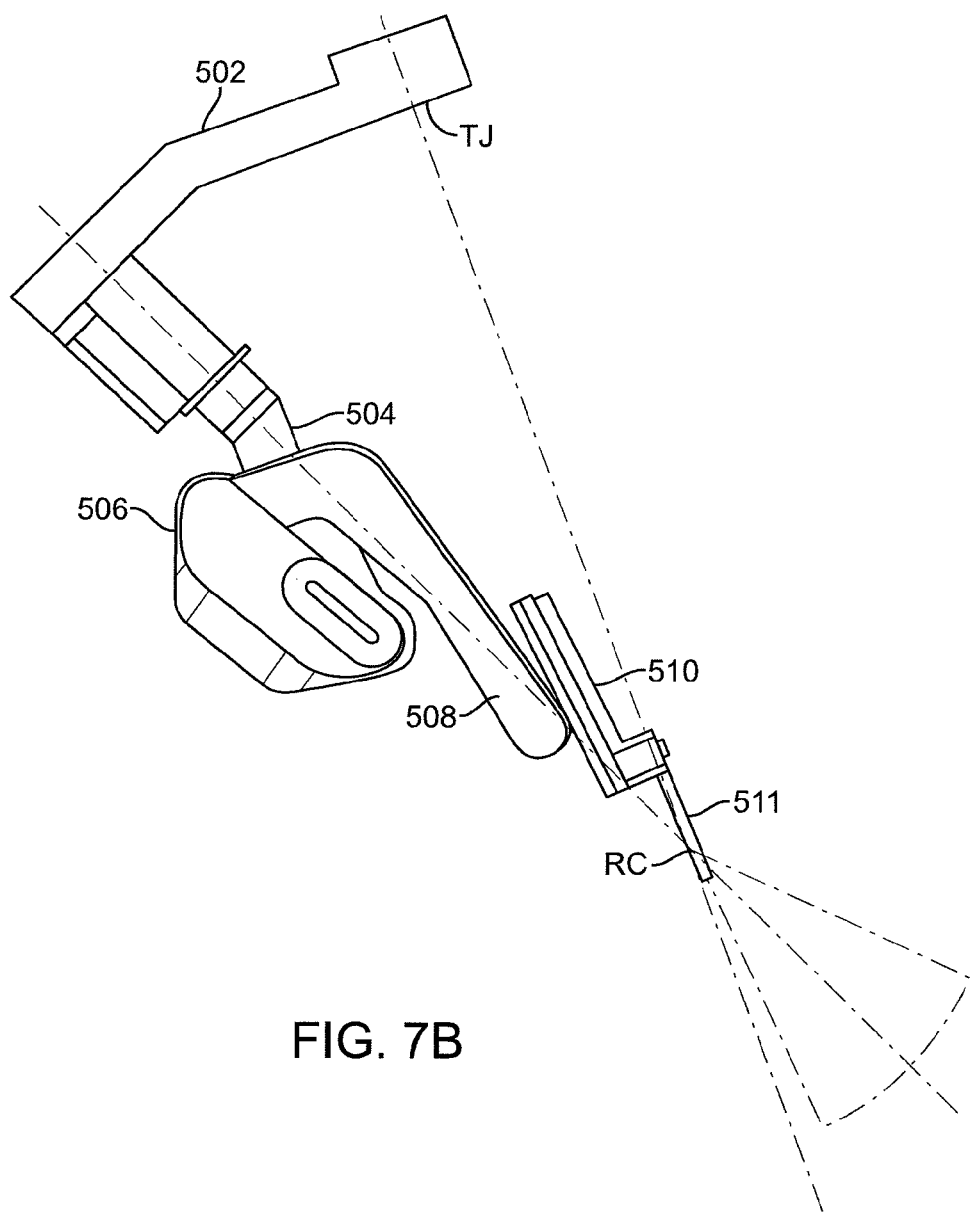
FIG. 7B shows an example manipulator arm and the associated range of motion and cone of silence, the example manipulator arm having a proximal revolute joint that revolves the manipulator arm around an axis of a proximal revolute joint the movement of which can be used to mitigate the depicted cone of silence.

FIGS. 7A-7B illustrate an additional redundant joint for use with example manipulator arms—a first joint coupling a proximal portion of the manipulator arm to the base. The first joint is a proximal revolute joint TJ that revolves the manipulator arm about a joint axis of joint TJ. The proximal revolute TJ includes a link 501 that offsets joint J1 from the proximal revolute TJ by a pre-detemined distance or angle. The link 501 can be a curved linkage, as shown in FIG. 7A, or a linear or angled linkage, as shown in FIG. 7B. Typically, the joint axis of the joint TJ is aligned with the remote center RC or insertion point of the tool tip, as shown in each of FIG.

7A. In an example embodiment, the joint axis of joint TJ passes through the remote center, as does each other revolute joint axis in the manipulator arm, to prevent motion at the body wall and can therefore be moved during surgery. The axis of joint TJ is coupled to a proximal portion of the arm so it can be used to change the position and orientation of the back of the arm. In general, redundant axes, such as this, allow the instrument tip to follow the surgeon's commands while simultaneously avoiding collisions with other arms or patient anatomy. In one aspect, the proximal revolute TJ is used solely to change the mounting angle of the manipulator with respect to the floor. This angle is important in order to 1) avoid collisions with external patient anatomy and 2) reach anatomy inside the body. Typically, the angle a between the proximal link of the manipulator attached to the proximal revolute joint TJ and the axis of the proximal revolute is about 15 degrees.

FIG. 7B illustrates the relationship of the proximal revolute joint TJ and its associated joint axis and the cone of silence in an example manipulator arm. The joint axis of the proximal revolute joint TJ may pass through the cone of silence or may be completely outside of the cone of silence. By revolving the manipulator arm about the axis of the proximal revolute TJ, the cone of silence can be reduced (in an embodiment where the joint TJ axis passes through the cone of silence), or can be effectively eliminated (in an embodiment where the proximal revolute joint axis extends completely outside the cone of silence). The distance and angle of the link 501 determines the position of the joint TJ axis relative to the cone of silence.

Figure 8:
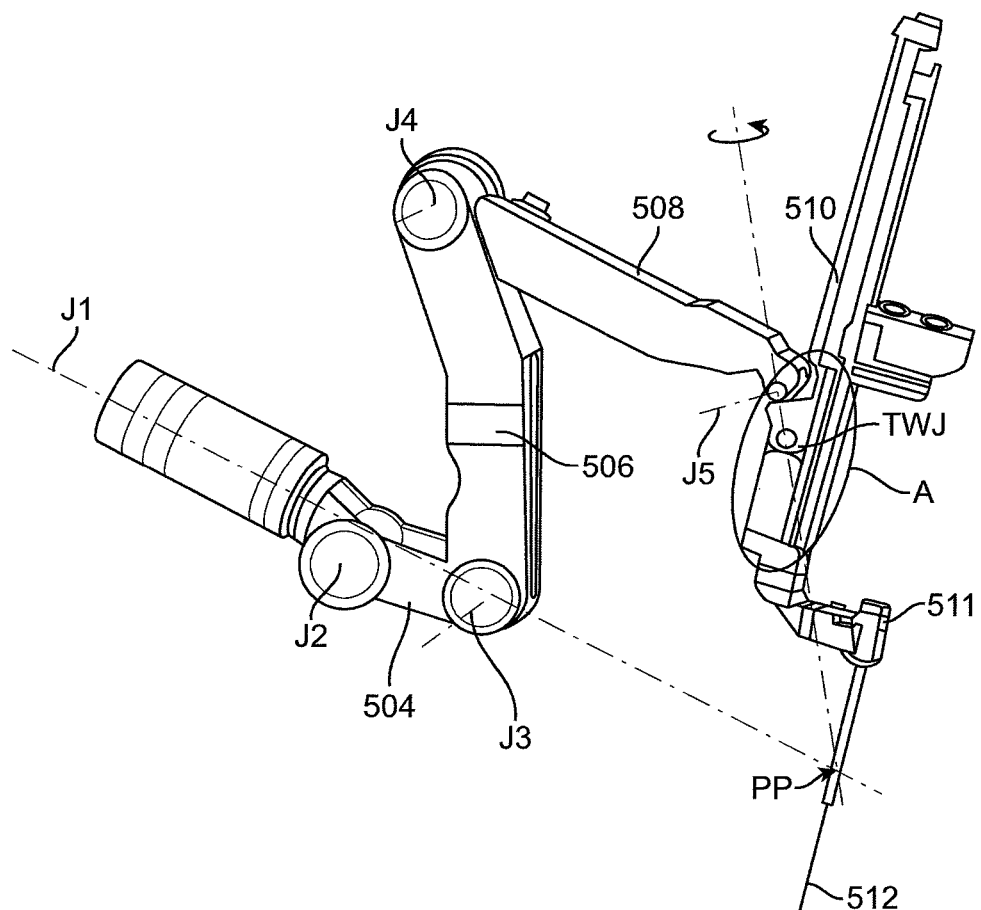
FIG. 8 shows an example manipulator arm having a revolute joint near the distal instrument holder.
Figure 9:
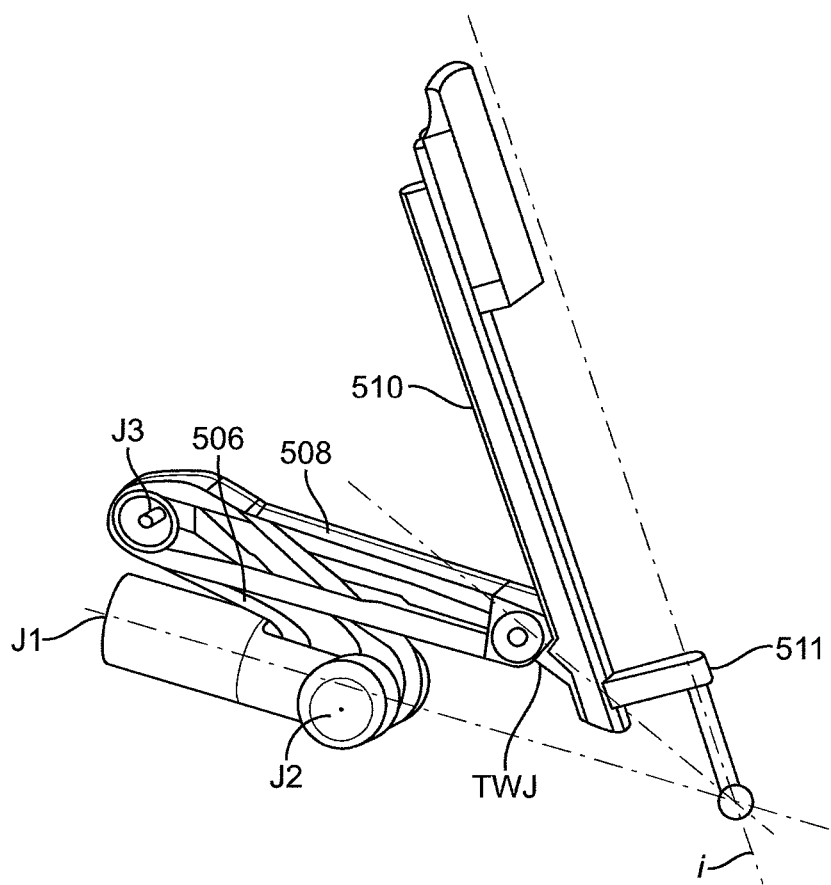
FIG. 9 shows an example manipulator arm having a revolute joint near the distal instrument holder that revolves or twists the instrument holder about the joint axis.
Figure 10A:
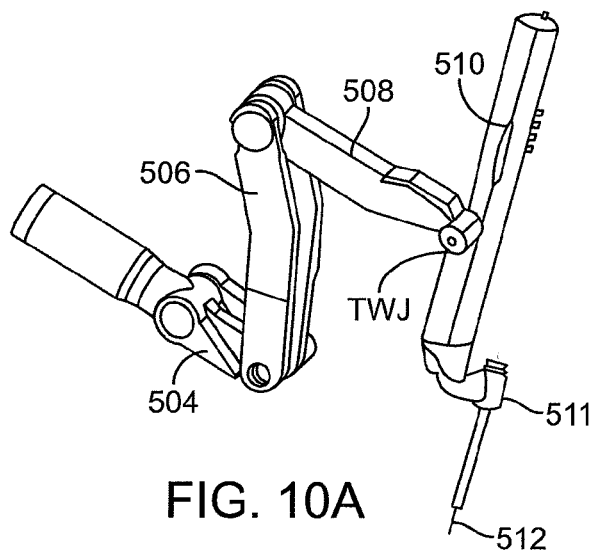
FIGS. 10A-10C show sequential views of an example manipulator arm having a revolute joint near a distal instrument holder as the joint is moved throughout its range of joint movement.
Figure 10B:
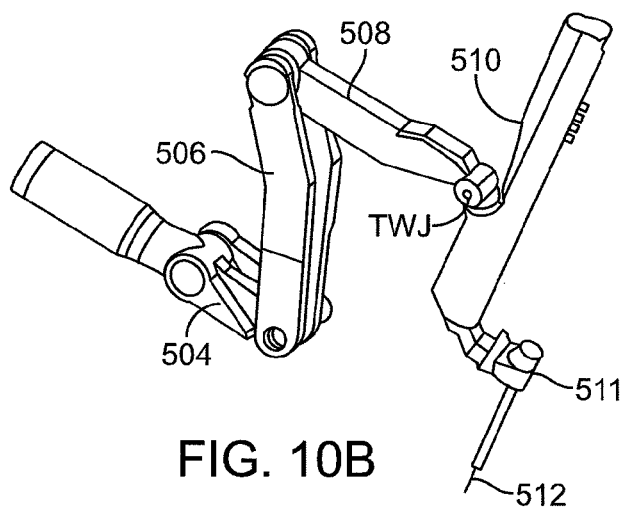
Figure 10C:
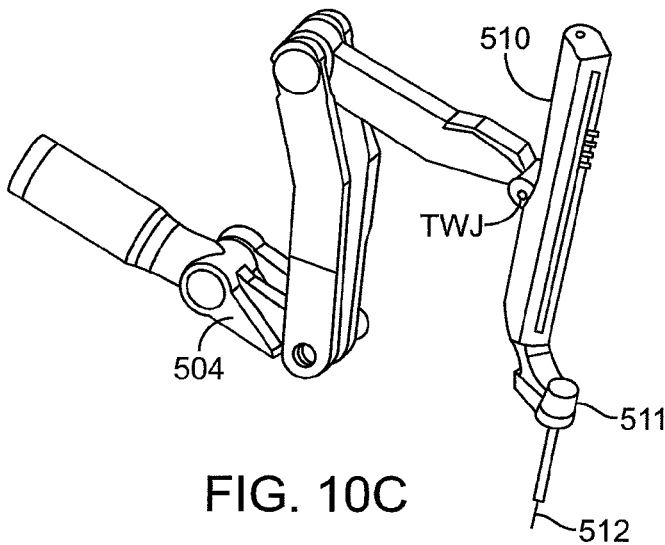

FIG. 8 illustrates another type of redundant joint for use with example manipulator arms, a distal revolute joint TWJ coupling the instrument holder 510 to a distal link of the manipulator arm 508. The distal revolute joint TWJ allows the system to twist the instrument holder 510 about the joint axis, which typically passes through the remote center or insertion point. Ideally, the revolute joint is located distally on the arm and is therefore particularly well suited to moving the orientation of the insertion axis. The addition of this redundant axis allows the manipulator to assume multiple positions for any single instrument tip position. In general, redundant axes, such as this, allow the instrument tip to follow the surgeon's commands while simultaneously avoiding collisions with other arms or patient anatomy. Because the distal revolute joint TWJ has the ability to move the insertion axis closer to the yaw axis, it is able to increase arm pitch back range of motion. The relationship between the axis of the distal revolute joint TWJ, the yaw axis of J1 and the insertion axis of tool tip is shown in FIG. 9. FIGS. 10A-10C show the sequential movement of the TWJ and how it shifts the insertion axis of tool tip from side to side.

Figure 11A:
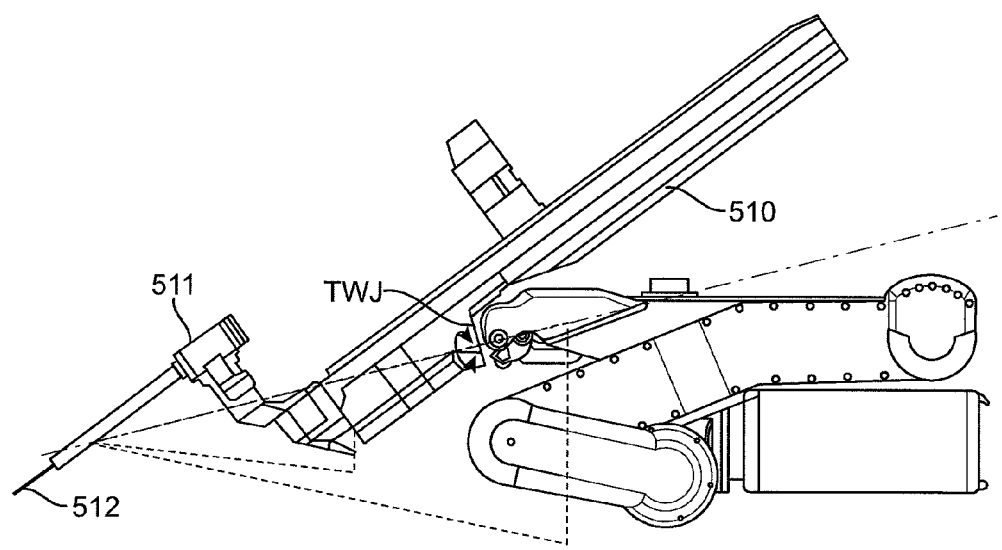
FIGS. 11A-11B show the revolved profile of an example manipulator arm having a distal revolute joint when the angular displacement of the joint is 0° versus an angular displacement of 90°, respectively.
Figure 11B:
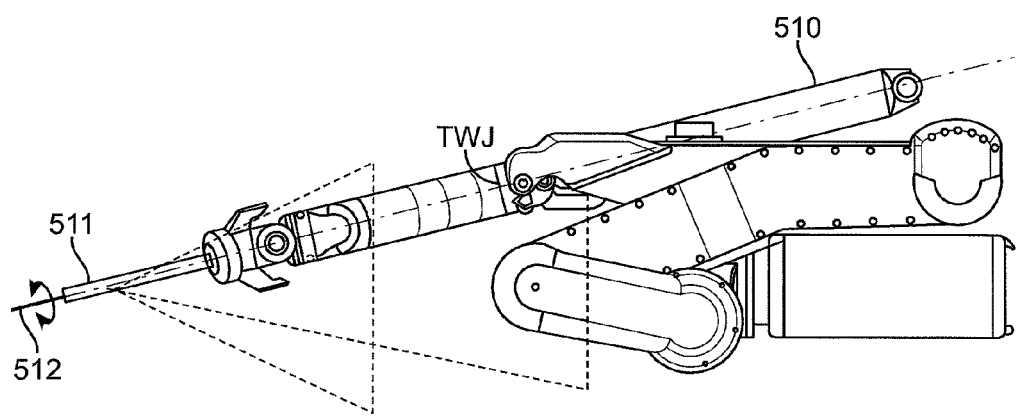
Figure 12A:
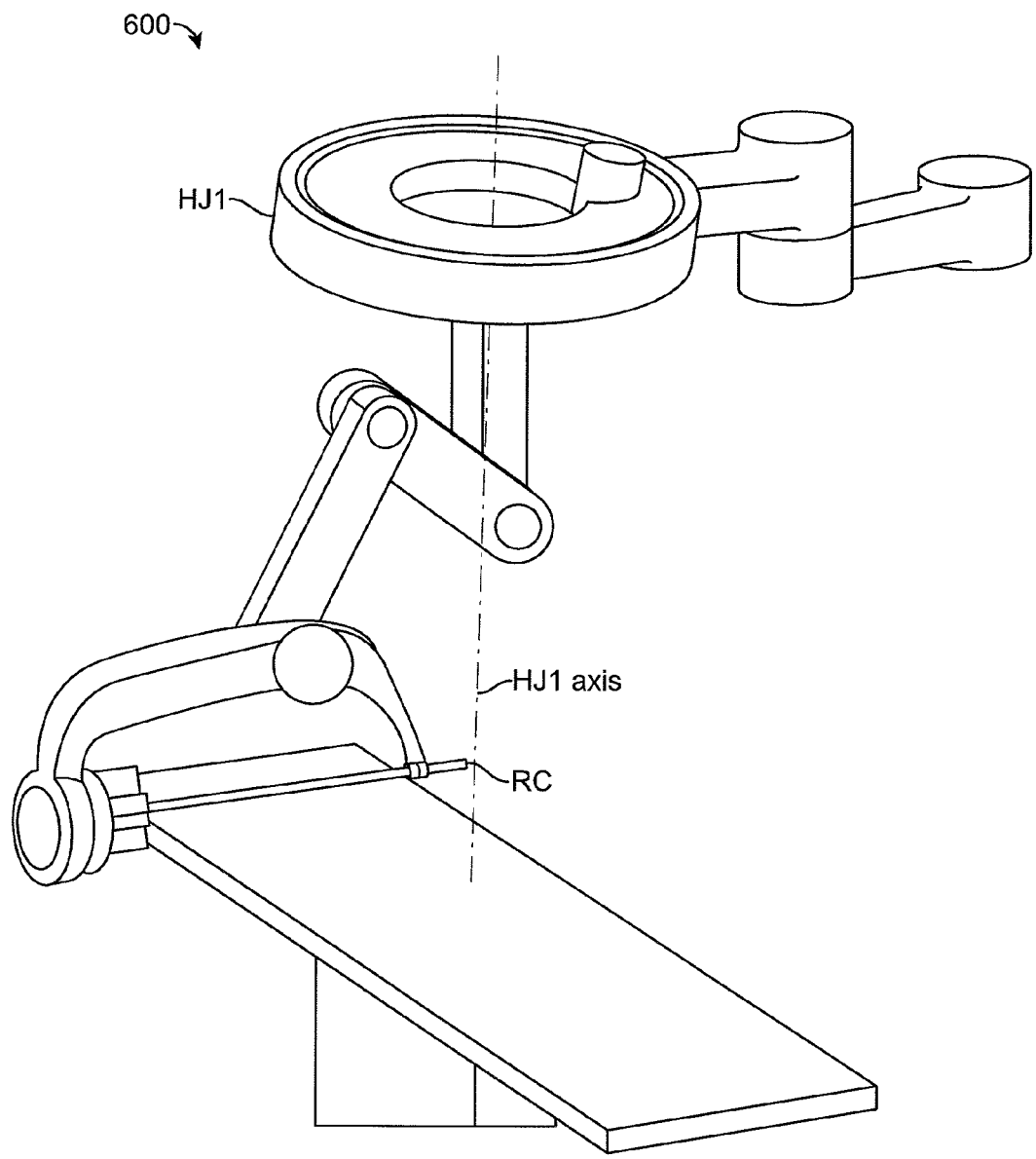
Figure 12B:
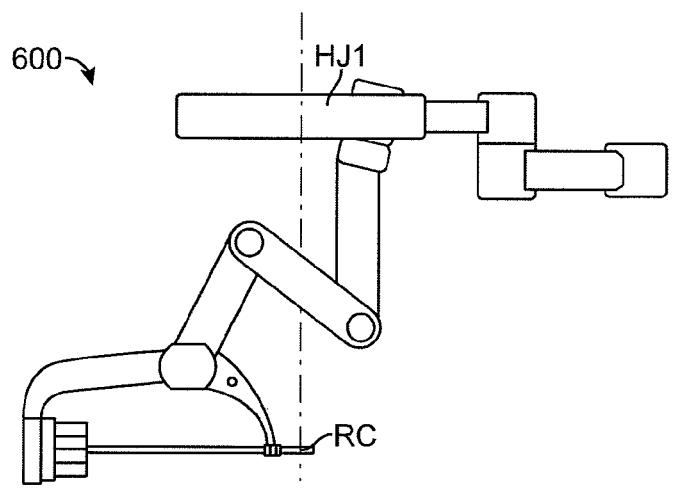
Figures 12C, 12D:
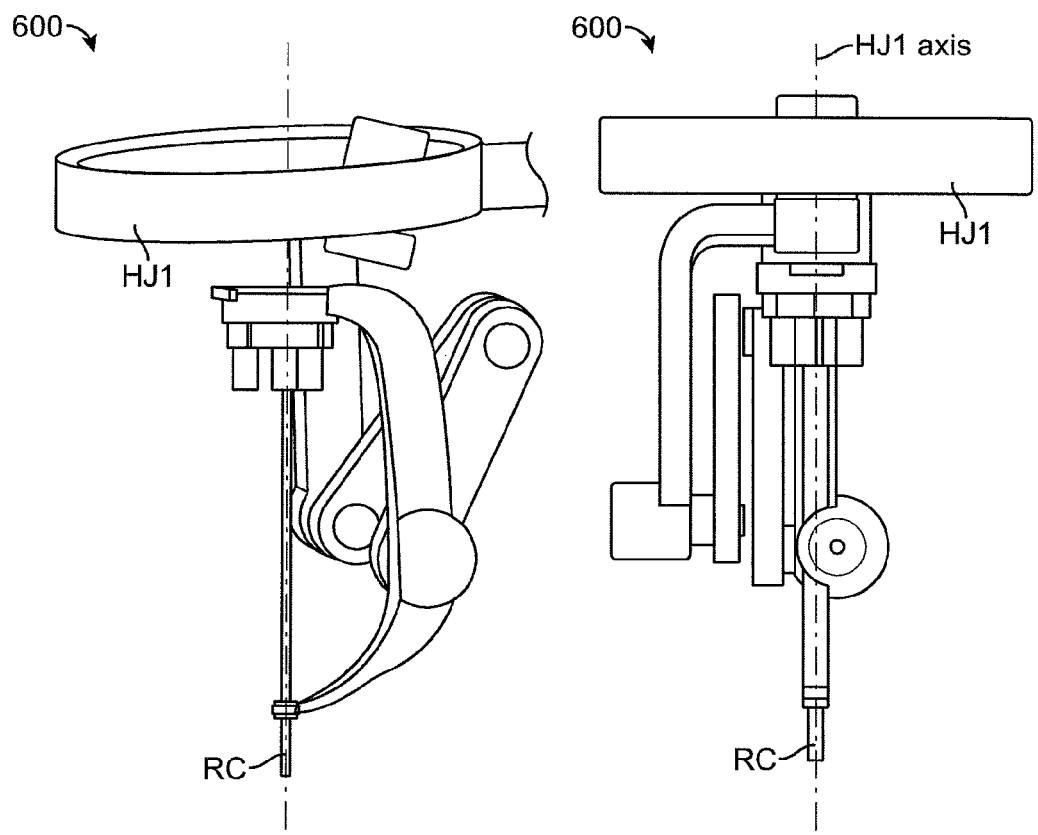

Another advantage of the distal revolute joint TWJ is that it may reduce the patient clearance cone, which is the swept volume of the distal portion of the manipulator arm proximal of the insertion point which must clear the patient to avoid collision between the patient and the instrument holder or distal linkages of the manipulator arm. FIG. 11A illustrates the patient clearance cone of the proximal portion of the manipulator arm while the angular displacement of the distal revolute joint remains at 0°. FIG. 11B illustrates the reduced patient clearance cone of the proximal portion of the manipulator arm while the distal revolute joint is shown having an angular displacement of 90° about its axis. Thus, in procedures having minimal patient clearance near the insertion point, use of the joint TWJ in accordance with the present invention may provide additional clearance while maintaining the remote center location or the position of the end effector as desired.

FIGS. 12A-13C illustrate another type of redundant joint for use with example manipulator arms, a proximal joint that translates or revolves the manipulator arm about an axis. In certain embodiments, this proximal translatable joint translates a proximal joint of the manipulator, such as joint J1 or TJ, along a path so as to reduce or eliminate the cone of silence by shifting or rotating the range of motion of the manipulator arm to provide for better conditioning and improved maneuverability of the manipulator arm. The translatable joint may include a circular path, such as shown in joint HJ1 in FIGS. 12A-12D, or may include a semi-circular or arcuate path, such as shown in FIGS. 13A-13C. Generally, the joint revolves the manipulator arm about an axis of the translatable joint that intersects with the remote center RC about which the shaft of the tool 512 extending through cannula 511 pivots. In the embodiment shown in FIGS. 12A-12D, this axis of HJ1 is a vertical axis, whereas in the embodiment shown in FIGS. 13A-13C the axis of HJ2 is horizontal.

In example embodiments, the manipulator arm 500 may include any or all of the a proximal or distal revolute joint, a proximal translatable joint and a parallelogram configuration of the distal linkages. Use of any or all of these features provide additional redundant degrees of freedom and facilitate reconfiguration in accordance with the present invention so as to provide for a better "conditioned" manipulator assembly by increasing the angles between linkages thereby improving the dexterity and motion of the manipulator. The increased flexibility of this example manipulator can also be used to optimize the kinematics of the manipulator linkage so as to avoid joint limits, singularities, and the like.

In an example embodiment, the joint movements of the manipulator are controlled by driving one or more joints by a controller using motors of the system, the joints being driven according to coordinated and joint movements calculated by a processor of the controller. Mathematically, the controller may perform at least some of the calculations of the joint commands using vectors and/or matrices, some of which may have elements corresponding to configurations or velocities of the joints. The range of alternative joint configurations available to the processor may be conceptualized as a joint space. The joint space may, for example, have as many dimensions as the manipulator has degrees of freedom, and a particular configuration of the manipulator may represent a particular point in the joint space, with each coordinate corresponding to a joint state of an associated joint of the manipulator.

In an example embodiment, the system includes a controller in which a commanded position and velocity of a feature in the work-space, denoted here as its Cartesian-coordinate space (referred to herein as Cartesian-space), are inputs. The feature may be any feature on the manipulator or off the manipulator which can be used as a control frame to be articulated using control inputs. An example of a feature on the manipulator, used in many examples described herein, would be the tool-tip. Another example of a feature on the manipulator would be a physical feature which is not on the tool-tip, but is a part of the manipulator, such as a pin or a painted pattern. An example of a feature off the manipulator would be a reference point in empty space which is exactly a certain distance and angle away from the tool-tip. Another example of a feature off the manipulator would be a target tissue whose position relative to the manipulator can be established. In all these cases, the end effector is associated with an imaginary control frame which is to be articulated using control inputs. However, in the following, the "end effector" and the "tool tip" are used synonymously. Although generally, there is no closed form relationship which maps a desired Cartesian space end effector position to an equivalent joint-space position, there is generally a closed form relationship between the Cartesian space end effector and joint-space velocities. The kinematic Jacobian is the matrix of partial derivatives of Cartesian space position elements of the end effector with respect to joint space position elements. In this way, the kinematic Jacobian captures the kinematic relationship between the end effector and the joints. In other words, the kinematic Jacobian captures the effect of joint motion on the end effector. The kinematic Jacobian (J) can be used to map joint-space velocities (dq/dt) to Cartesian space end effector velocities (dx/dt) using the relationship below:

$$dx/dt = J\, dq/dt$$

Thus, even when there is no closed-form mapping between input and output positions, mappings of the velocities can iteratively be used, such as in a Jacobian-based controller to implement a movement of the manipulator from a commanded user input, however a variety of implementations can be used. Although many embodiments include a Jacobian-based controller, some implementations may use a variety of controllers that may be configured to access the Jacobian of the manipulator arm to provide any of the features described herein.

One such implementation is described in simplified terms below. The commanded joint position is used to calculate the Jacobian (J). During each time step ($\Delta t$) a Cartesian space velocity (dx/dt) is calculated to perform the desired move ($dx_{des}/dt$) and to correct for built up deviation ($\Delta x$) from the desired Cartesian space position. This Cartesian space velocity is then converted into a joint-space velocity (dq/dt) using the pseudo-inverse of the Jacobian ($J^\#$). The resulting joint-space commanded velocity is then integrated to produce joint-space commanded position (q). These relationships are listed below:

$$dx/dt = dx_{des}/dt + k\Delta x \quad (1)$$

$$dq/dt = J^\# dx/dt \quad (2)$$

$$q_i = q_{i-1} + dq/dt\, \Delta t \quad (3)$$

The pseudo-inverse of the Jacobian (J) directly maps the desired tool tip motion (and, in some cases, a remote center of pivotal tool motion) into the joint velocity space. If the manipulator being used has more useful joint axes than tool tip degrees of freedom (up to six), (and when a remote center of tool motion is in use, the manipulator should have an additional 3 joint axes for the 3 degrees of freedom associated with location of the remote center), then the manipulator is said to be redundant. A redundant manipulator's Jacobian includes a "null-space" having a dimension of at least one. In this context, the "null-space" of the Jacobian (N(J)) is the space of joint velocities which instantaneously achieves no tool tip motion (and when a remote center is used, no movement of the pivotal point location); and "null-motion" is the combination, trajectory or path of joint positions which also produces no instantaneous movement of the tool tip and/or location of the remote center. Incorporating or injecting the calculated null-space velocities into the control system of the manipulator to achieve the desired reconfiguration of the manipulator (including any reconfigurations described herein) changes above equation (2) to the following:

$$dq/dt = dq_{perp}/dt + dq_{null}/dt \quad (4)$$

$$dq_{perp}/dt = J^\# dx/dt \quad (5)$$

$$dq_{null}/dt = (1 - J^\# J)z = V_n V_n^T z = V_n \alpha \quad (6)$$

The joint velocity according to Equation (4) has two components: the first being the null-perpendicular-space component, the "purest" joint velocity (shortest vector length) which produces the desired tool tip motion (and when the remote center is used, the desired remote center motion); and the second being the null-space component. Equations (2) and (5) show that without a null-space component, the same equation is achieved. Equation (6) starts with a traditional form for the null-space component on the left, and on the far right side, shows the form used in an example system, wherein ($V_n$) is the set of orthonormal basis vectors for the null-space, and ($\alpha$) are the coefficients for blending those basis vectors. In some embodiments, $\alpha$ is determined by control parameters, variables or setting, such as by use of knobs or other control means, to shape or control the motion within the null-space as desired.

Figure 14A:
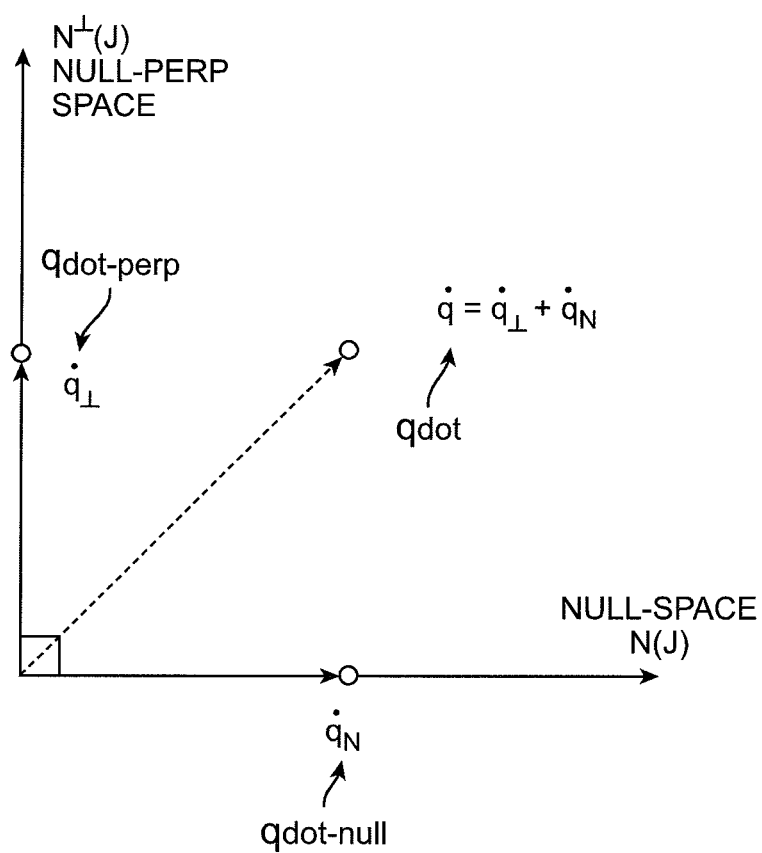
FIGS. 14A-14B graphically represent the relationship between the null-space and the null-perpendicular-space of the Jacobian of an example manipulator assembly.

FIG. 14A graphically illustrates the relationship between the null-space of the Jacobian and the null-perpendicular-space of the Jacobian of an example manipulator arm. FIG. 14A shows a two-dimensional schematic showing the null-space along the horizontal axis, and the null-perpendicular-space along the vertical axis, the two axes being orthogonal to one another. The diagonal vector represents the sum of a velocity vector in the null-space and a velocity vector in the null-perpendicular-space, which is representative of Equation (4) above.

Figure 14B:
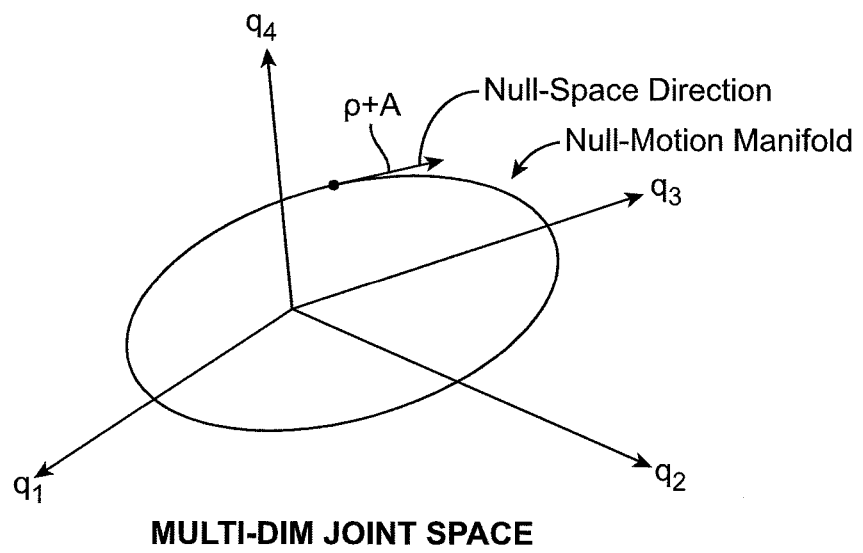

FIG. 14B graphically illustrates the relationship between the null-space and the null-motion manifold within a four-dimensional joint space, shown as the "null-motion manifold." Each arrow (q1, q2, q3, and q4) represents a principal joint axis. The closed curve represents a null-motion manifold which is a set of joint-space positions that instantaneously achieves the same end effector position. For a given point A on the curve, since the null-space is a space of joint velocities that instantaneously produces no movement of the end effector, the null-space is parallel to the tangent of the null-motion manifold at point A.

Figure 15A:
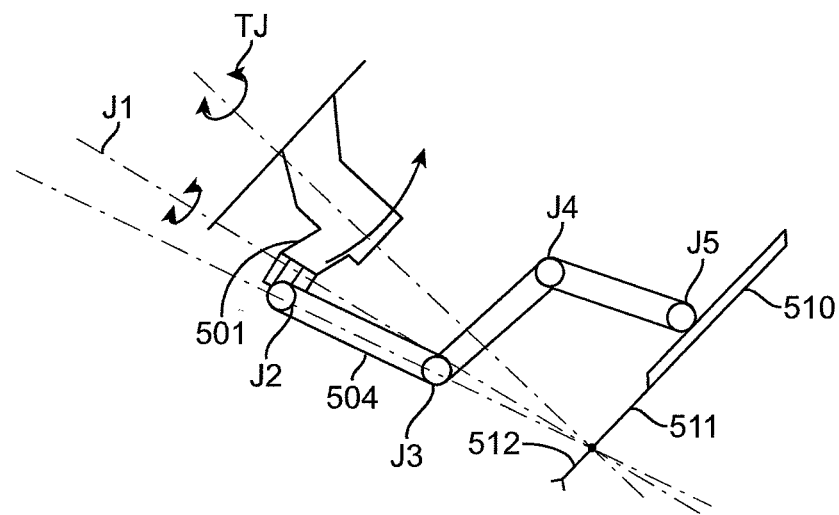
FIGS. 15A-15B illustrate reconfiguration of an example manipulator assembly for a given end effector position.
Figure 15B:
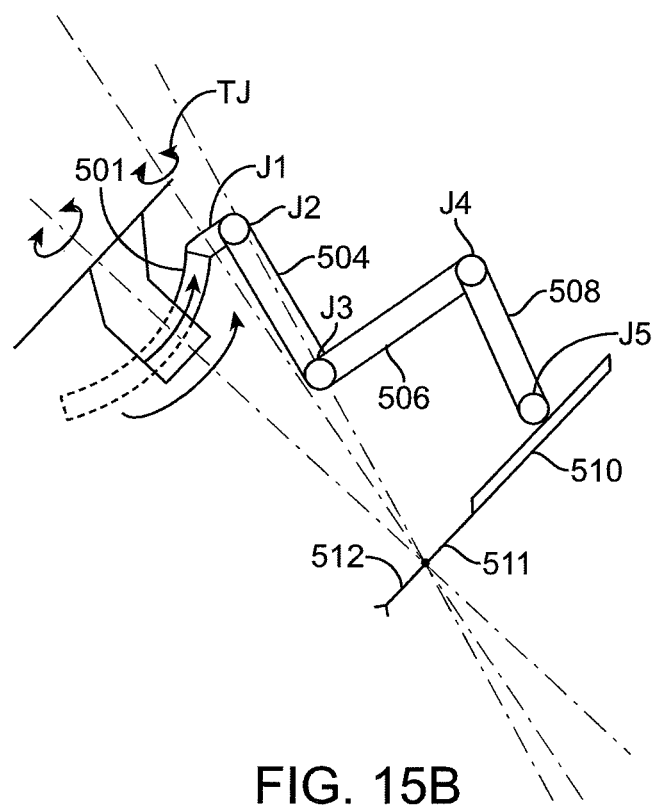
Figure 16A:
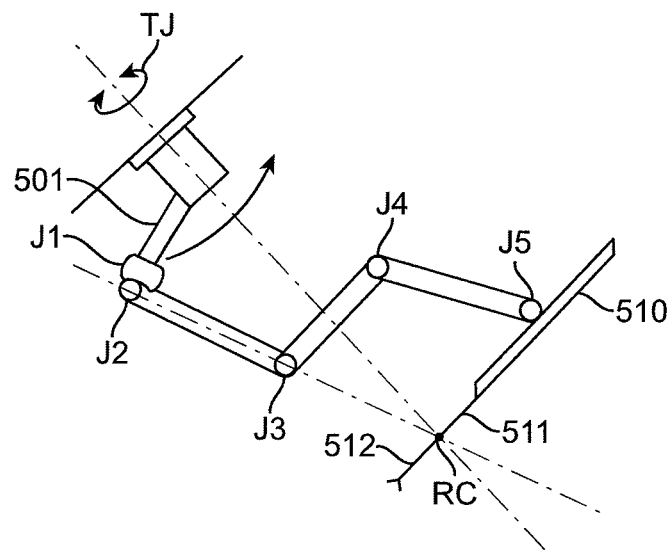
FIGS. 16A-16B illustrate an example manipulator for a given remote center location at which an associated instrument shaft pivots.
Figure 16B:
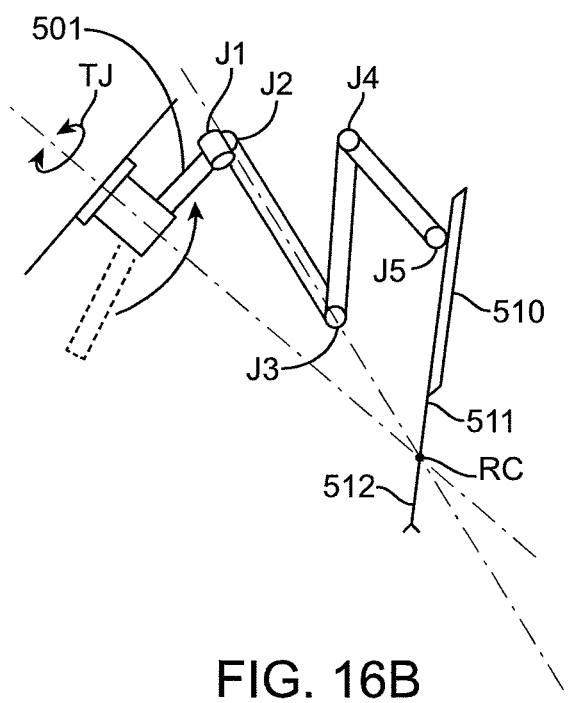

FIGS. 15A-15B schematically illustrate an example manipulator 500 before and after reconfiguring of the manipulator arm by driving the joints of the manipulator within the null space. In FIG. 15A, in response to a reconfiguration command entered by a user, the system drives the joint TJ counter-clockwise within the null-space for the given position of the end effector of instrument and according to the calculated movement of the remaining joints, the coordinated movements of the remaining joints within the null-space having been calculated by the system. The null-space joint velocities are injected into the system so as to maintain the given state of the end effector, thereby enabling the user to reconfigure the manipulator as desired, even during movement of the end effector during a surgical procedure. In another aspect, the system may calculate the velocities of the joints within the null-space of the Jacobian so as to effect the desired configuration while the structural design of the manipulator arm maintains the remote center location, such as in the embodiment shown in FIGS. 16A-16B.

In some embodiments, one or more joints of the manipulator arm may be constrained such that the one or more joints are not driven within the null-space to effect reconfiguration, however such joints may still be driven within the null-perpendicular-space to effect a desired movement of the end effector. Alternatively, one or more joints, such as the a proximal revolute joint, may be constrained so that the one or more joints are not driven to effect a desired movement of the end effector, but are driven to effect reconfiguration movement of the manipulator. In other embodiments, the controller may be configured such that the velocity of the joints driven within the null-space is limited or held at a substantially constant speed for a duration of the reconfiguration command. In still other embodiments, the system may be configured such that the velocities of the joints within the null-space are scaled according to the joint location and/or configuration, or any number of conditions. For example, a user may desire the proximal most joints be driven with a higher velocity than the more distal joints in the manipulator arm during reconfiguration movement. Additionally, the system may be configured so as to maintain a position or state of any one of the joints of the manipulator arm as desired.

Figure 17A:
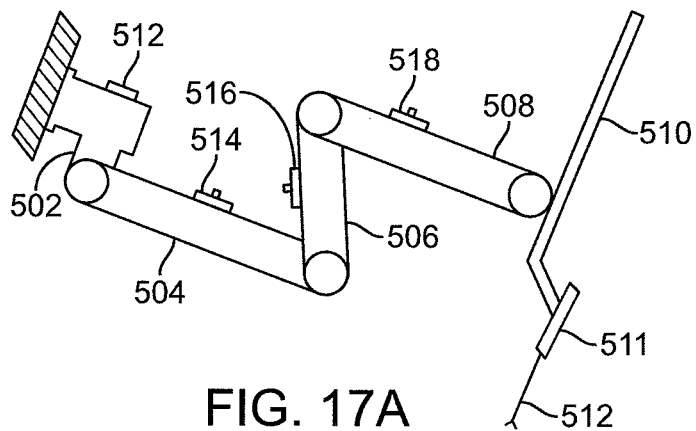
FIGS. 17A-17C illustrate three examples of manipulation command inputs in accordance with many embodiments.
Figure 17B:
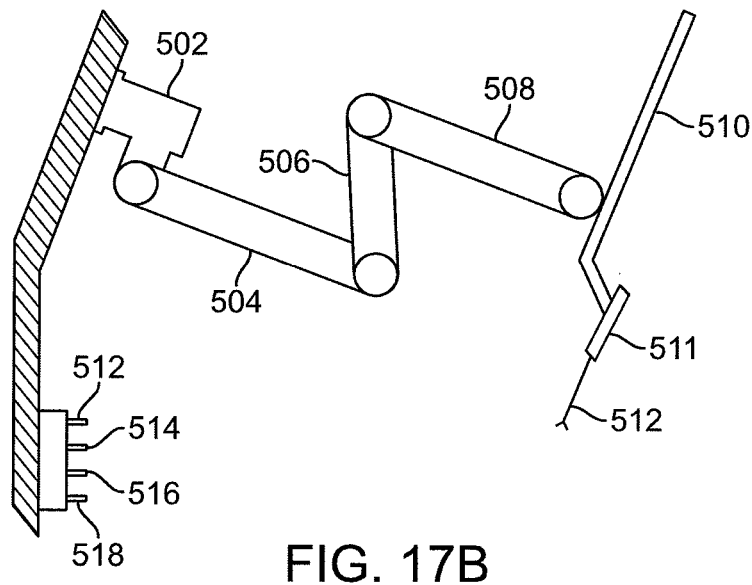
Figure 17C:
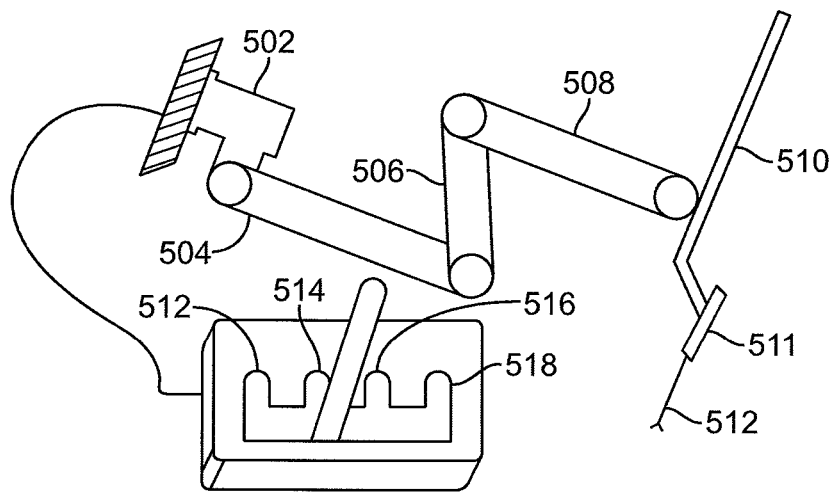

In another aspect, the system may receive the reconfiguration command from a system user in any number of ways. In certain embodiments, the manipulator includes an input device for receiving a reconfiguration command from a user. The input device may include one or more buttons or mechanisms for driving one or more joints as desired (or alternatively for moving one or more links) and may be disposed on the manipulator arm, preferably in a location corresponding to the joint driven in response to activation of the device, such as in FIG. 17A. Alternatively, the system may include an input device having a cluster of buttons or mechanisms, each corresponding to a joint or linkage of the manipulator arm, such as that shown in the embodiment of FIG. 17B. This embodiment allows a user to reconfigure the arm from a centralized location. The input device may also comprise a joystick, such as in FIG. 17C, that may be operated to drive one or more joints and effect reconfiguration as desired. It is appreciated that the input device may include any number of variations.

Figure 18A:
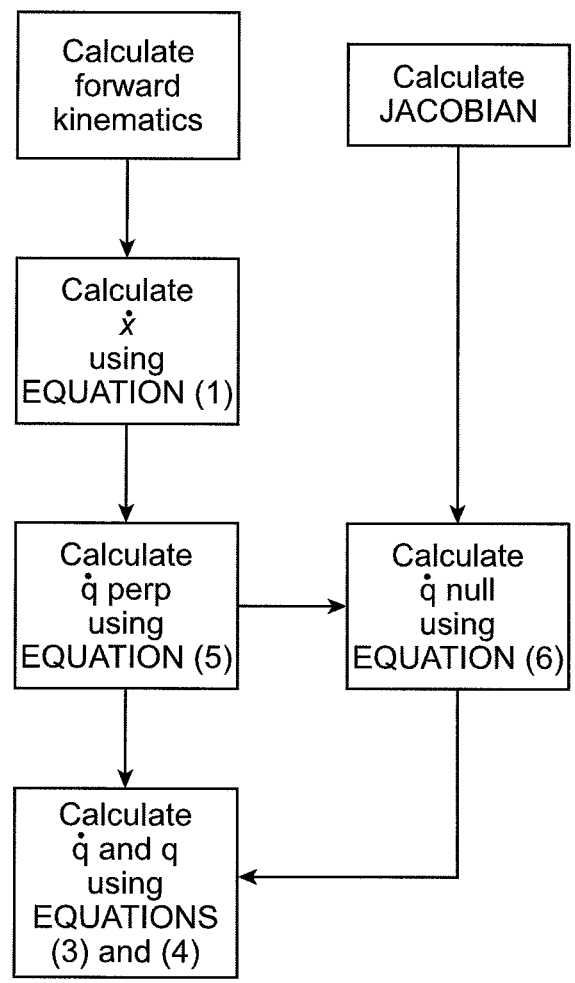
FIGS. 18A-18B are simplified block diagram representing methods in accordance with many embodiments.
Figure 18B:
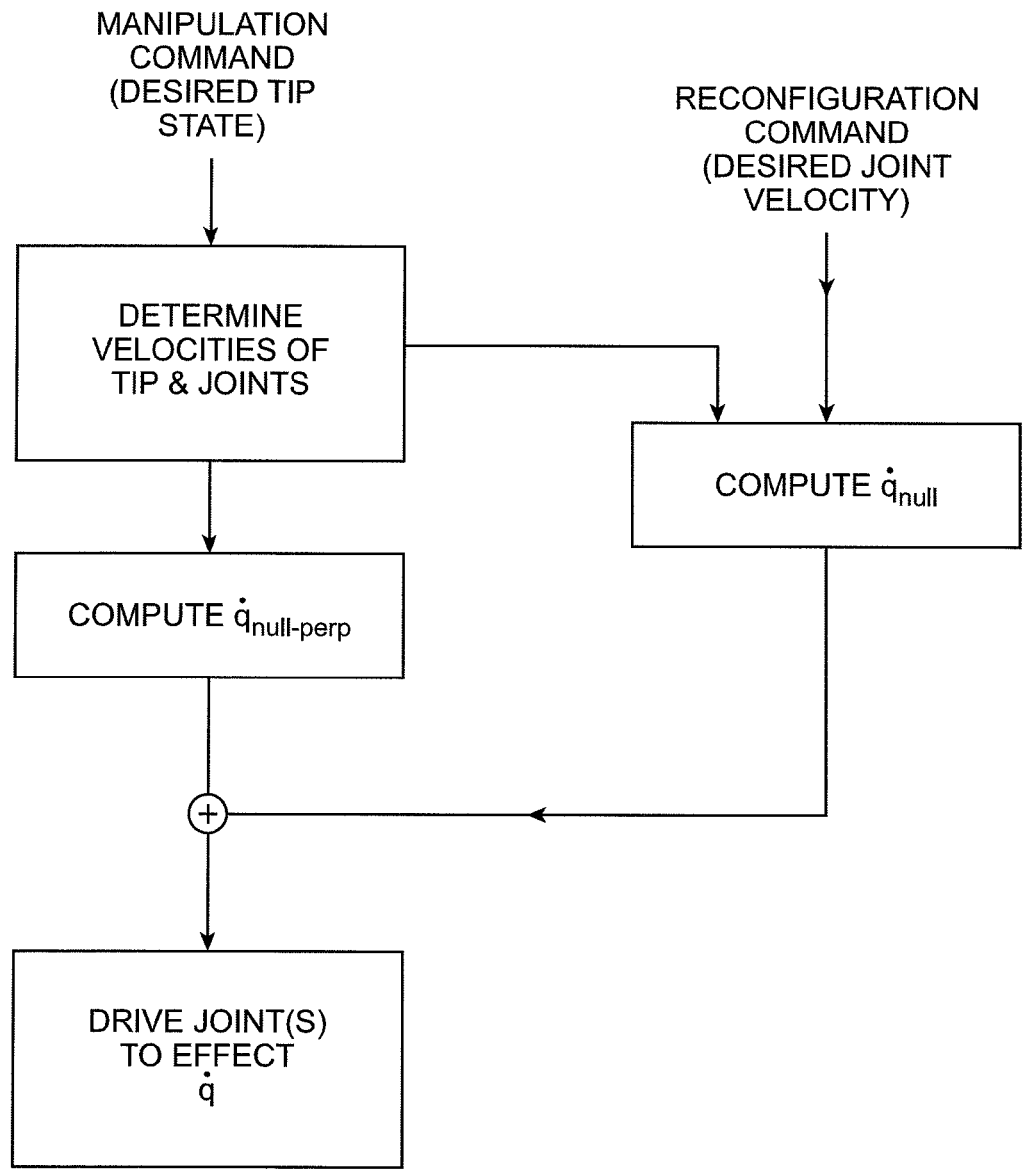

FIGS. 18A-18B illustrate methods of reconfiguring a manipulator assembly of a robotic surgical system in accordance with many embodiments of the present invention. FIG. 18A shows a simplified schematic of the required blocks need to implement the general algorithms to control the patient side cart joint states, in relation to the equations discussed above. According to the method of FIG. 18A, the system: calculates the forward kinematics of the manipulator arm; then calculates dx/dt using Equation (1), calculates $dq_{perp}/dt$ using Equation (5), and then calculates $dq_{null}/dt$ from z which may depend on $dq_{perp}/dt$ and the Jacobian using Equation (6). From the calculated $dq_{perp}/dt$ and $dq_{null}/dt$, the system then calculates dq/dt and q using Equations (4) and (3), respectively, thereby providing the movement by which the controller can effect the desired reconfiguration of the manipulator while maintaining the desired state of the end effector and/or location of the remote center.

FIG. 18B shows a block diagram of an example embodiment of the system. In response to a manipulation command, which commands a desired tool tip state, the system determines the velocities of the tool tip and the states of the joints from which the $dq_{perp}/dt$ is calculated. In response to receiving a reconfiguration command from a user, a processor can use the determined tool tip and joint velocities (or the calculated $dq_{perp}/dt$) to calculate the $dq_{null}/dt$, after which the system adds the velocities into the calculated dq/dt so as to drive the joint(s) of the system and effecting the desired movement (or state) of the end effector and reconfiguration of the manipulator arm.

While the example embodiments have been described in some detail for clarity of understanding and by way of example, a variety of adaptations, modifications, and changes will be obvious to those of skill in the art. Hence, the scope of the present invention is limited solely by the appended claims.

What is claimed is:

1. A robotic system comprising:
   a manipulator arm configured for robotically moving a distal portion relative to a proximal base, the manipulator arm having a plurality of joints between the distal portion and a proximal portion coupled to the proximal base, the plurality of joints providing sufficient degrees of freedom to allow a range of joint states of the plurality of joints for a given state of the distal portion;
   an input device configured for receiving a reconfiguration command to move a first one or more joints of the plurality of joints for a desired reconfiguration movement of a first portion of the manipulator arm between the proximal base and the distal portion so as to maintain a desired state of the distal portion in combination with the reconfiguration movement of the first portion of the manipulator arm; and
   a processor coupling the input device to the manipulator arm, the processor being configured to calculate, in response to the reconfiguration command, velocities of the plurality of joints for a first movement of the plurality of joints to move the first one or more joints of the plurality of joints in accordance with the reconfiguration command, the calculated velocities of the plurality of joints being within a null-space of a Jacobian of the manipulator arm and including a component corresponding to the first one or more joints of the plurality of joints, and the processor being further configured to drive the plurality of joints according to the first movement so as to maintain the desired state of the distal portion in combination with the reconfiguration movement of the first portion of the manipulator arm.

2. The robotic system of claim 1 further comprising:
   an input device for receiving a manipulation command to move the distal portion for a desired distal portion movement, wherein the processor is further configured to calculate a distal portion displacing movement of the plurality of joints in response to the manipulation command, wherein the calculating of the distal portion displacing movement of the plurality of joints comprises calculating joint velocities within a null-perpendicular-space of the Jacobian, the null-perpendicular-space being orthogonal to the null-space, and wherein the processor is further configured to drive the plurality of joints according to the calculated distal portion displacing movement of the plurality of joints so as to effect the desired distal portion movement.

3. The robotic system of claim 2, wherein the processor is further configured to calculate the distal portion displacing movement of the plurality of joints so that the first one or more joints are not driven.

4. The robotic system of claim 2, wherein the processor is further configured to calculate the first movement of the plurality of joints so that the first one or more joints are not driven to effect the distal portion displacing movement of the plurality of joints.

5. The robotic system of claim 1, wherein the processor is further configured to calculate the first movement of the plurality of joints so that a movement of a first joint of the first one or more joints provides a substantially constant speed of the first joint for a duration of the first movement.

6. The robotic system of claim 1, wherein the input device for receiving the reconfiguration command is disposed on a portion of the manipulator arm such that entering the reconfiguration command with the input device drives a joint of the plurality of joints adjacent the portion of the manipulator arm on which the input device is disposed so as to move the portion of the manipulator arm on which the input device is disposed.

7. The robotic system of claim 1, wherein the input device for receiving the reconfiguration command comprises a button cluster, and wherein the button cluster comprises a plurality of buttons, each button of the plurality of buttons corresponding to a different joint of the plurality of joints.

8. The robotic system of claim 1, wherein the input device for receiving the reconfiguration command comprises a joystick configured such that two or more of the plurality of joints are selectively driveable by movement of the joystick.

9. The robotic system of claim 2, further comprising a user interface that includes a surgeon console and a patient side cart, wherein the input device for receiving the reconfiguration command and the input device for receiving the manipulation command are configured so that each is disposed on one of the patient side cart or the surgeon console.

10. The robotic system of claim 1, wherein the proximal portion of the manipulator arm is coupled to the proximal base by a first joint from the first one or more joints.

11. The robotic system of claim 1, wherein the proximal portion of the manipulator arm is coupled to the proximal base by a first joint of the plurality of joints such that the proximal portion of the manipulator arm is moveable relative to the proximal base while joints are driven according to the reconfiguration movement.

12. The robotic system of claim 10, wherein the first joint is a revolute joint that supports the plurality of joints of the manipulator arm such that joint movement of the revolute joint pivots one or more joints of the plurality of joints about a pivotal axis of the revolute joint, the pivotal axis extending from the revolute joint through the distal portion.

13. The robotic system of claim 12, wherein joint movement of the revolute joint pivots one or more joints of the plurality of joints about an axis oriented towards a remote center of motion.

14. The robotic system of claim 11, wherein the first joint is moveable relative to the base along an arcuate or substantially circular path such that movement of the first joint along the path pivots one or more joints of the plurality of joints about an axis extending through a remote center of motion.

15. The robotic system of claim 1, wherein the distal portion comprises a surgical instrument having an elongate shaft extending distally to a surgical end effector, wherein the shaft pivots about a remote center of motion during surgery, and wherein the movement of the plurality of joints is calculated so as to maintain a position of the shaft at the remote center of motion in combination with the reconfiguration movement of the first portion of the manipulator arm.

16. The robotic system of claim 1, wherein the distal portion is configured to support a surgical instrument having an elongate shaft extending distally to a surgical end effector, wherein the shaft pivots about a remote center of motion during surgery, and wherein the movement of the plurality of joints is calculated so as to maintain a position of the shaft at the remote center of motion in combination with the reconfiguration movement of the first portion of the manipulator arm.

17. The robotic system of claim 1, wherein the distal portion comprises a tool, the tool including an intermediate portion extending along an insertion axis distally from the proximal portion and an end effector at a distal end of the intermediate portion, wherein two or more of the plurality of joints mechanically constrain movement of the distal portion relative to the proximal base such that movement of the end effector at a work site is facilitated as the distal portion of the manipulator arm pivots about a remote center of motion located along the insertion axis.

18. The robotic system of claim 1, wherein the distal portion is configured to support a tool, the tool including an intermediate portion extending along an insertion axis distally from the proximal portion and an end effector at a distal end of the intermediate portion, wherein two or more of the plurality of joints mechanically constrain movement of the distal portion relative to the proximal base such that movement of the end effector at a work site is facilitated as the distal portion of the manipulator arm pivots about a remote center of motion located along the insertion axis.

19. The robotic system of claim 1, wherein the desired state of the distal portion comprises at least one of a position, orientation, or velocity relative to the proximal base.

20. The robotic system of claim 1, wherein
the distal portion comprises an end effector relative to a proximal base;
the manipulator arm comprises a plurality of links that are kinematically joined by one or more joints of the plurality of joints; and
the first movement of the plurality of joints moves at least one link of the plurality of links for the desired reconfiguration movement of the first portion of the manipulator arm between the proximal base and the distal portion comprising the end effector.

21. The robotic system of claim 20 further comprising:
an input device for receiving a manipulation command to move the end effector for a desired end effector movement, the input device being disposed on a user interface, wherein the processor is further configured to calculate an end effector displacing movement of the plurality of links in response to the manipulation command, wherein calculating the end effector displacing movement of the plurality of links comprises calculating joint velocities within a null-perpendicular-space of the Jacobian, the null-perpendicular-space being orthogonal to the null-space, and wherein the processor is further configured to drive the one or more joints kinematically coupling the plurality of links according to the calculated end effector displacing movement of the plurality of links to effect the desired end effector movement.

22. The robotic system of claim 20, wherein a first link of the plurality of links of the manipulator arm is joined to the proximal base by a joint such that the first link is moveable relative to the proximal base while the links are moved according to the reconfiguration movement.

23. The robotic system of claim 22, wherein the joint coupling the first link to the base is a revolute joint that supports the one or more joints of the manipulator arm such that joint movement of the revolute joint pivots one or more links of plurality of links of the manipulator arm about a pivotal axis of the revolute joint, the pivotal axis extending from the revolute joint toward the end effector.

24. The robotic system of claim 20, wherein the desired state of the distal portion comprises at least one of a position, orientation, or velocity relative to the proximal base for the end effector included in the distal portion.

25. The robotic system of claim 1, wherein
the distal portion includes a surgical instrument having a proximal end, a distal end effector suitable for insertion into a patient, and an intermediate portion having an insertion axis therebetween;
the manipulator arm is configured to support the proximal end of the surgical instrument so as to pivot the surgical instrument from outside the patient, wherein the plurality of joints comprises remote center joints configured to mechanically constrain movement of the surgical instrument included in distal portion to pivot about a remote center pivot point along the insertion axis and adjacent to a minimally invasive aperture; and
the first movement of the plurality of joints maintains the intermediate portion at the pivot point in combination with the reconfiguration movement of the first portion of the manipulator arm, the maintenance of the intermediate portion at the pivot point corresponding to the desired state of the distal portion.

26. The robotic system of claim 25 further comprising:
an input device for receiving a manipulation command to move the end effector for a desired end effector movement, the input device for receiving the manipulation command being disposed on a user interface and being separate from the input device for receiving the reconfiguration command, wherein the processor is further configured to calculate an end effector displacing movement of the plurality of joints in response to the manipulation command, wherein calculating end effector displacing movement of the plurality of joints comprises calculating joint velocities within a null-perpendicular-space of the Jacobian, the null-perpendicular-space being orthogonal to the null-space, and wherein the processor is further configured to drive the plurality of joints according to the calculated end effector displacing movement of the plurality of joints to effect the desired end effector movement and maintain the intermediate portion at the pivot point.

27. The robotic system of claim 26, wherein the processor is further configured to calculate joint movement so that the first one or more joints of the plurality of joints is not driven when calculating the end effector displacing movement of the plurality of joints.

28. The robotic system of claim 25, wherein the processor is further configured to calculate joint movement so that a first joint from the first one or more joints of the plurality of joints provides a substantially constant speed of the first joint for a duration of the reconfiguration command.

29. The robotic system of claim 25, wherein the input device for receiving the reconfiguration command is disposed on a portion of the manipulator arm such that entering a command with the input device drives an adjacent joint so as to move the portion of the manipulator arm on which the input device is located.

30. The robotic system of claim 25, wherein the input device for receiving the reconfiguration command comprises a button cluster, wherein the button cluster comprises a plurality of buttons, each button corresponding to a different joint of the plurality of joints.

31. The robotic system of claim 25, wherein the input device for receiving the reconfiguration command comprises a joystick such that the plurality of joints are selectively driveable by movement of the joystick.

32. The robotic system of claim 25, wherein a proximal portion of the manipulator arm is coupled to the proximal base by a first joint of the one or more joints.

33. The robotic system of claim 32, wherein the first joint is a revolute joint that supports the plurality of joints of the manipulator arm such that joint movement of the revolute joint pivots one or more joints of the plurality of joints about a pivotal axis of the revolute joint, the pivotal axis extending from the revolute joint through the remote center pivot point.

34. The robotic system of claim 25, wherein the desired state of the distal portion comprises at least one of a position, orientation, or velocity relative to the proximal base for the intermediate portion of the surgical instrument included in the distal portion.

35. The robotic system of claim 1, wherein
the distal portion includes a surgical instrument having a proximal end, a distal end effector suitable for insertion into a patient, and an intermediate portion extending along an insertion axis therebetween;
the manipulator arm is configured to support the proximal end of the surgical instrument so as to move the surgical instrument from outside the patient so that the intermediate portion pivots about a remote center, wherein the manipulator arm includes a plurality of links that are kinematically joined by the plurality of joints, some of the plurality of links comprising remote center links coupled together by remote center joints configured to mechanically constrain movement of the insertion axis to a rotation about first and second remote center axes traversing the insertion axis extending through the remote center;
the first movement of the plurality of joints moves at least one link of the plurality of links for the desired reconfiguration movement of the first portion of the manipulator arm between the proximal base and the distal portion, the input device being coupled with the manipulator so that the plurality of joints are driven in accordance with the desired reconfiguration movement in response to the reconfiguration command while maintaining a desired state of the surgical instrument included in the distal portion, wherein driving the plurality of joints pivotally moves the insertion axis of the surgical instrument supported by the distal portion about a first set of joint axes, the first set of joint axes traversing the insertion axis through the remote center, and the first set of joint axes being angularly offset from the first and second remote center axes.

36. The robotic system of claim 35, wherein the processor is configured to calculate a reconfiguration movement of the plurality of links within the null-space of the Jacobian of the manipulator arm in response to a reconfiguration command for the plurality of links.

37. The robotic system of claim 36 further comprising:
an input device for receiving a manipulation command to move the end effector for a desired end effector movement, the input device for receiving the manipulation command being disposed on a user interface and being separate from the input device for receiving the reconfiguration command;
wherein the processor is further configured to calculate an end effector displacing movement of the plurality of links in response to the manipulation command, wherein calculating end effector displacing movement of the plurality of links comprises calculating velocities of the plurality of joints within a null-perpendicular-space of the Jacobian, the null-perpendicular-space being orthogonal to the null-space, and wherein the processor is further configured to move the plurality of links according to the calculated end effector displacing movement by driving one or more of the plurality of joints kinematically coupling the links to effect the desired end effector movement.

38. The robotic system of claim 36, wherein the user interface comprises a surgeon console and a patient side cart, the input device for the manipulation command being disposed on the surgeon console and the input device for the reconfiguration command being disposed on the patient side cart.

39. The robotic system of claim 36, wherein the user interface comprises a surgeon console and a patient side cart, the input device for the manipulation command being disposed on the surgeon console and the input device for the reconfiguration command being disposed on the surgeon console.

40. The robotic system of claim 36, wherein the user interface comprises a surgeon console and a patient side cart, the input device for the manipulation command being disposed on the patient side cart and the input device for the reconfiguration command being disposed on the patient side cart.

41. The robotic system of claim 35, wherein a proximal portion of the manipulator arm is coupled to the proximal base by a joint such that the proximal portion of the manipulator arm is moveable relative to the proximal base when the links are moved according to the reconfiguration movement.

42. The robotic system of claim 41, wherein the joint coupling the proximal portion to the base is a revolute joint that supports the links of the manipulator arm such that joint movement of the revolute joint pivots one or more of the plurality of links of the manipulator arm about a pivotal axis of the revolute joint, the pivotal axis extending from the revolute joint toward the remote center.

43. The robotic system of claim 35, wherein the desired state of the distal portion comprises at least one of a position, orientation, or velocity relative to the proximal base for the intermediate portion of the surgical instrument included in the distal portion.

* * * * *